United States Patent [19]

Peters et al.

[11] Patent Number: 5,116,865
[45] Date of Patent: May 26, 1992

[54] 15,16-SECO-19-NOR PROGESTINS

[76] Inventors: Richard H. Peters, 365 Springpark Cir., San Jose, Calif. 95136; Masato Tanabe, 972 Moreno Ave., Palo Alto, Calif. 94303

[21] Appl. No.: 647,298

[22] Filed: Jan. 28, 1991

Related U.S. Application Data

[63] Continuation-in-part of Ser. No. 578,091, Sep. 5, 1990, abandoned.

[51] Int. Cl.$^5$ .................. A61K 31/21; C07C 69/013; C07C 255/45
[52] U.S. Cl. .................... 514/510; 558/427; 558/429; 560/256; 568/373; 564/308
[58] Field of Search ............... 560/256; 514/510, 511; 558/429, 427; 568/373; 564/308

[56] References Cited

U.S. PATENT DOCUMENTS

| | | | |
|---|---|---|---|
| 3,109,009 | 10/1963 | Nomine et al. | 260/397.4 |
| 3,206,472 | 9/1965 | Nagata | 260/326.3 |
| 3,275,691 | 9/1966 | Goldberg et al. | 260/586 |
| 3,471,550 | 10/1969 | Uskokovic | 260/488 |

OTHER PUBLICATIONS

J. S. Baran, *J. Med. Chem.* 10(6):1039–1047 (1967).
M. A. Bielfeld et al., *J. Med. Chem.* 12(1):192–195 (1969).
P. F. Sherwin et al., *J. Med. Chem.* 32(3):651–657 (1989).

*Primary Examiner*—Howard T. Mars
*Assistant Examiner*—Kimberly J. Kestler
*Attorney, Agent, or Firm*—Dianne E. Reed

[57] ABSTRACT

15,16-Seco-19-nor progestins are provided which display elevated progestational activity with a minimum of ancillary hormonal activity. Processes for the preparation of the novel progestins are provided as are methods of use. A preferred method of use is in the suppression of ovulation in the human female.

11 Claims, No Drawings

15,16-SECO-19-NOR PROGESTINS

ORIGIN OF THE INVENTION

This invention was made with U.S. government support under Contract No. N-01-HD-1-2809 awarded by the National Institutes of Health. The U.S. Government has certain rights in this invention.

CROSS-REFERENCE TO RELATED APPLICATIONS

This application is a continuation-in-part of U.S. patent application Ser. No. 07/578,091, filed Sep. 5, 1990, now abandoned.

1. Technical Field

The present invention is in the field of steroid chemistry. More particularly it relates to novel 15,16-seco-19-nor progestins, as well as their preparation and methods of use. The novel compounds possess potent progestational activity with a minimum of ancillary hormonal activity.

2. Background of the Invention

The use of substituted steroids for a number of therapeutic purposes, e.g., in the control of conception in female mammals in the regulation of the menstrual cycle, in conjunction with chemotherapy, and for a number of other purposes, has been known for some time. See, for example, G. Pincus et al., Science 124:890 (1956); J. Rock et al., Science 124:891 (1956); G. Pincus, *The Control of Fertility*, (New York: Academic Press, 1965); and C. Djerassi, Science 151: 3716 (1966).

The present invention is specifically directed to novel progestins, i.e., synthetic progesterone-like compounds which have no natural counterpart in the human body. These compounds find a wide range of beneficial applications in human therapy. Such applications include, for example, in addition to suppressing ovulation in the human female, control of uterine bleeding, treatment of amenorrhea and dysmenorrhea, alleviation of endocrine disorders, and treatment of infertility. Examples of progestins and progestogens (i.e., naturally occurring progesterone-like compounds) which have been used for these purposes include but are not limited to acetoxypregnenolone, anagestone acetate, chlormadinone acetate, desogestrol, dimethisterone, ethisterone, ethynodiol diacetate, fluorogestone acetate, gestodene,. hydroxymethylprogesterone and derivatives thereof (e.g., hydroxymethylprogesteroneacetate),hydroxyprogesteroneand derivatives thereof (e.g., hydroxyprogesterone acetate and hydroxy- progesterone caproate), levonorgestrel, lynestenol, melengestrol acetate, norethindrone, norethindrone acetate, norgesterol, normethisterone, pregnenolone, and progesterone.

Insofar as contraceptive methods and compositions are concerned, progestins are components of both the sequential and combination "pill" as well as long-acting injectables. Progestins are also administered together with an estrogenic component for the treatment of climacteric disturbances. See, e.g.: U.S. Pat. No. 3,836,651 to Rudel et al.; U.S. Pat. No. 3,932,635 to Segre; U.S. Pat. No. 3,969,502 to Lachnit-Fixson; and U.S. Pat. No. 4,145,416 to Lachnit-Fixson et al. (Progestins have also been used in oral contraceptive as in U.S. Pat. No. 3,822,355 to Kincl et al. and in 4,066,757 to Pasquale. Indeed, such a formulation, containing norethindrone, is currently available and marketed under the trade- name "Nor-Q.D." by Syntex Corporation, Palo Alto, Calif.)

While there are thus a number of progestins commercially available, with or without accompanying estrogenic compounds, there is a continuing need to improve efficacy and safety while minimizing unwanted side effects. Perhaps the most serious of these side effects is ancillary hormonal activity, i.e., androgenic. estrogenic and antiestrogenic activities as well as inhibition of adrenocortical function. The following table illustrates the androgenic, estrogenic, and antiestrogenic effects of currently available contraceptive formulations:

TABLE 1

| Pill | Progestin | Androgenic Effect |
|---|---|---|
| Ovcon-35 | 0.4 mg norethindrone | 0.14 |
| Brevicon/Modiçon | 0.5 mg norethindrone | 0.17 |
| Demulen 1/35 | 1 mg ethynodiol diacetate | 0.21 |
| Tri-Norinyl | 0.5, 1.0, 0.5 mg norethindrone | 0.24 |
| Ortho-Novum 7/7/7 | 0.5, 0.75, 1 mg norethidrone | 0.26 |
| Ortho-Novum 10/11 | 0.5, 1 mg norethindrone | 0.26 |
| Triphasil/Tri-Levlen | 0.5, 0.075, 0.12 mg levonorgestrel | 0.29 |
| Norinyl and Ortho 1/35 | 1 mg norethindrone | 0.34 |
| Nordette/Levlen | 0.15 mg levonorgestrel | 0.47 |
| Lo/Ovral | 0.30 mg norgestrel | 0.47 |
| Loestrin 1/20 | 1 mg norethindrone acetate | 0.52 |
| Loestrin 1/5/30 | 1.5 mg norethindrone acetate | 0.52 |

| Progestin | Estrongenic Effect |
|---|---|
| Norgestrel (Ovral, Lo/Ovral, Nordette, Tri-Levlen, Levlen) | 0.00 |
| Norethindrone (1 mg) (Norinyl and Ortho-Novum) | 1.00 |
| Norethindrone acetate (1 mg) (Norlestrin) | 1.52 |
| Ethynodiol diacetate (1 mg) (Demulen and Ovulen) | 3.44 |
| Norethynodrel (2.5 mg) (Enovid) | 20.80 |

| Progestin | Anti-Estrongenic Effect |
|---|---|
| Norethynodrel (2.5 mg) (Enovid) | 0.0 |
| Ethynodiol diacetate (1 mg) (Demulen and Ovulen) | 1.0 |
| Norethindrone (1 mg) (Norinyl and Ortho-Novum) | 2.5 |
| Norgestrel (0.5 mg) (Ovral) | 18.5 |
| Norethindrone acetate (1 mg) (Norlestrin) | 25.0 |

(In Table 1, androgenic activity is expressed in terms of milligrams of methyl testosterone equivalents per 28 days based on a rat ventral prostate assay. The estrogenic effect values derive from a comparative potency test based on a rat vaginal epithelium assay. See R. C. Jones et al., "The Effects of Various Steroids on Vaginal Histology in the Rat," in *Fertil. Steril.* 24:284 (1973). See also R. P. Dickey, *Managing Contraceptive Pill Patients,* 4th Ed., Durant, Okl.: Creative Informatics, 1984.) The values for anti-estrogenic effect are calculated using the method of R. P. Dickey as set out in *Managing Contraceptive Pill Patients,* 4th ed., Turant, Okl.; Creative Information, Inc. (1984).

The ancillary hormonal activity of the above formulations is believed to be at least in part dose-related. Thus, it would be desirable to provide a novel progestin which has potent progestational activity with a minimum of ancillary hormonal activity.

3. Background Art

In addition to the references cited in the preceding section, the following patents and publications also relate to compounds, formulations, syntheses and methods of use which may be relevant herein.

D-Ring Modified Steroids: J. S. Baran, *J. Med. Chem.* 10(6):1039–47 (1967), describes the synthesis and chemistry of certain 15,16-seco steroids. P. F. Sherwin et al., in *J. Med. Chem.* 32(3):651–658 (1989), describe D-ring modification of androsta-1,4-diene-3,17-dione. U.S. Pat. No. 3,275,691 to Goldberg et al. describe polyhydrophenanthrene derivatives, i.e., in which the D-ring of the cyclopentanophenanthrene nucleus is open.

A-Ring Modified Steroids: U.S. Pat. Nos. 3,109,009 to Nomine et al. and 3,471,550 to Uskokovic et al. describe A-ring "seco" compounds.

Synthetic Methods: U.S. Pat. No. 3,206,472 to Nagata et al. describe a total synthesis of certain steroids which involves an intermediate having an "open" D-ring (compound XV in the patent).

SUMMARY OF THE INVENTION

It has now been discovered that certain novel 15,16-seco-19-nor progestins possess potent progestational activity, in some cases much higher than that of progesterone itself. The novel compounds presently disclosed and claimed also possess minimal ancillary hormonal activity and are thus far more desirable than the vast majority of progestins currently available. The present invention in one aspect provides these 15,16-seco-19-nor progestins as new chemical compounds within the classes defined by the following structural formulae (Ia), (Ib), (II), (IIa), (IIb), (IV), (Va), (Vb), (VI), (VII) and (VIII):

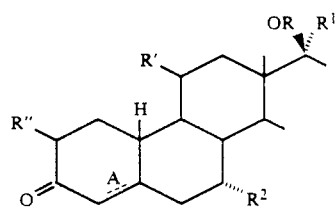
(Ia)

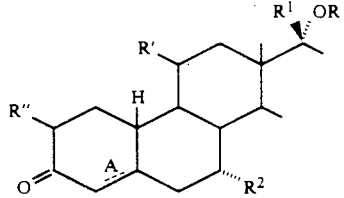
(Ib)

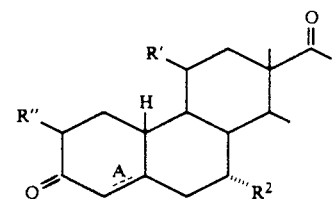
(II)

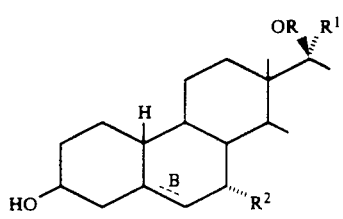
(IIIa)

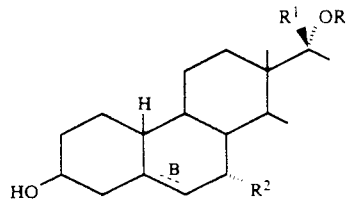
(IIIb)

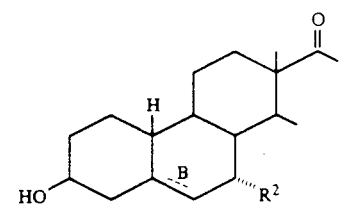
(IV)

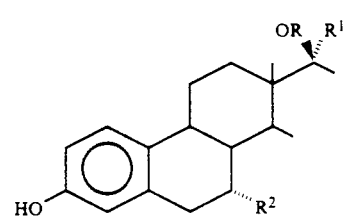
(Va)

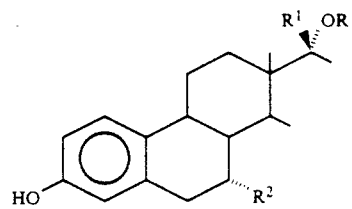
(Vb)

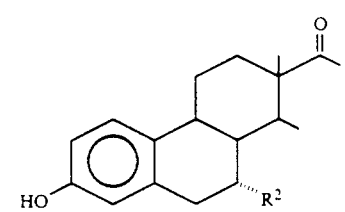
(VI)

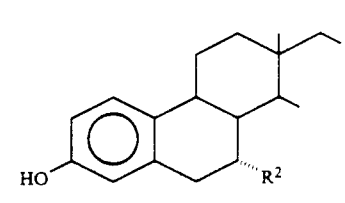
(VII)

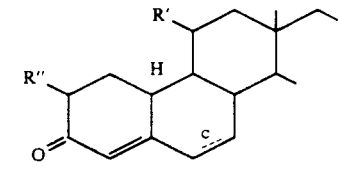
(VIII)

In these formulae:

R is hydrogen or an acyl group of the formula —(C=O)—Y;

Y is an organic substituent selected from the group consisting of alkyl, alkenyl, alkynyl, cycloalkyl, cycloalkylalkylene, haloalkyl, aryl, haloaryl and arylalkylene;

R' is hydrogen, alkyl of 1 to 12 carbon atoms, or

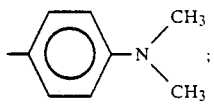

R" is hydrogen or lower alkyl;
R$^1$ is selected from the group consisting of hydrogen, alkyl, alkenyl and alkynyl;
R$^2$ is selected from the group consisting of hydrogen, lower alkyl, and cyano; and
A, B and C represent optional double bonds. The compounds having an asymmetric carbon atom at position 17 are provided herein in stereoisometrically pure form.

The invention also relates to a novel method of synthesizing certain of these compounds and to pharmaceutical compositions containing the novel compounds.

The invention further encompasses methods of treatment involving administration of one or more of the above compounds to a patient to achieve desired progestational effects. These methods of treatment involve administration of a composition containing a progestin as described herein within the context of a dosing regimen effective to achieve the intended therapeutic or prophylactic result. In a preferred embodiment, the progestin is administered in combination with a separate estrogenic component for purposes of controlling fertility in a mammalian female.

DETAILED DESCRIPTION OF THE INVENTION

Definitions

In this specification and in the claims which follow reference will be made to a number of terms which shall be defined to have the following meanings:

"Alkyl" refers to a branched or unbranched saturated hydrocarbon group of 1 to 24 carbon atoms, such as methyl, ethyl, n-propyl, isopropyl, n-butyl, isobutyl, t-butyl, octyl, decyl, tetradecyl, hexadecyl, eicosyl, tetracosyl and the like. Preferred "alkyl" groups herein contain 1 to 12 carbon atoms. "Lower alkyl" refers to an alkyl group of one to six, more preferably one to four, carbon atoms.

"Alkenyl" refers to a branched or unbranched unsaturated hydrocarbon group of 2 to 24 carbon atoms and one or more unsaturated carbon-carbon bonds, such as for example, ethenyl, 1-propenyl, 2-propenyl, 1-butenyl, 2-isobutenyl, octenyl, decenyl, tetradecenyl, Δ8,11-heptadecadienyl, hexadecenyl, eicosenyl, tetracosenyl and the like. "Lower alkenyl" refers to an alkenyl group of two to six, more preferably two to four, carbon atoms.

"Alkylene" refers to a difunctional saturated branched or unbranched hydrocarbon chain containing from 1 to 6 carbon atoms, and includes, for example, methylene (—CH$_2$), ethylene (—CH$_2$—CH$_2$), propylene (—CH$_2$—CH$_2$CH$_2$—), 2-methylpropylene [—CH$_2$—CH(CH$_3$)—CH$_2$—], hexylene [—(CH$_2$)$_6$—] and the like.

"Alkynyl" refers to a branched or unbranched acetylenically unsaturated hydrocarbon group of 2 to 24 carbon atoms such as ethynyl, 1-propynyl, 2-propynyl, 1-butynyl, 2-butynyl, octynyl, decynyl, tetradecenyl, hexadecynyl, and the like. "Lower alkynyl" refers to an alkynyl group of two to six, more preferably two to four carbon atoms.

"Acyl" refers to a group of the structure —(C=O)—Y, where Y is as described herein. Acyl, therefore, includes such groups as, for example, acetyl, propanoyl (or propionyl), isopropanoyl, n-butanoyl (or n-butyryl), octanoyl, eicosanoyl, propenoyl (or acryloyl), 2-methylpropenoyl (ormethacryloyl), octanoyl, tetradecenoyl, eicosenoyl, tetracosenoyl, propynoyl, 2-butynoyl, n-2-octynoyl, n-2-tetradecynoyl, 2-chloropentanoyl, 2-chlorotetracosanyl, 3-bromo-2-methacryloyl, benzoyl, 1- and 2- naphthoyl, phenylacetyl, 6-phenylhexylenoyl, and the like. "Lower acyl" refers to a —(C=O)—Y group wherein Y is a lower alkyl of one to six, more preferably one to four, carbon atoms such that the acyl contains a total of from two to seven, more preferably two to five, carbon atoms.

"Aryl" refers to a phenyl or 1- or 2-naphthyl group. Optionally, these groups are substituted with one to four, more preferably one to two, lower alkyl, lower alkoxy, hydroxy, and/or nitro substituents.

"Arylalkylene" refers to an aryl group as is defined herein which is attached to one end of an alkylene group as is defined herein. As used herein, the other end of the alkylene group is attached to the carbon of the carbonyl group to form the acyl group.

"Cycloalkyl" refers to a saturated hydrocarbon ring group having from 3 to 8 carbon atoms, and includes, for example, cyclopropyl, cyclobutyl, cyclohexyl, methylcyclohexyl, cyclooctyl, and the like.

"Cycloalkylalkylene" refers to a saturated hydrocarbon containing a cycloalkyl group as is defined herein attached to one end of an alkylene group as is defined herein. The term includes, for example, cyclopropylmethylene, cyclobutylethylene, 3-cyclohexyl-2-methylpropylene, 6-cyclooctylhexylene, and the like.

"Halo" or "halogen" refers to fluoro, chloro, bromo or iodo, usually regarding halo substitution for a hydrogen atom in an organic compound. Of the halos, chloro and bromo are generally preferred with chloro generally being the more preferred.

"Haloalkyl" refers to an "alkyl" group in which one to four, especially one of its hydrogen atoms, is substituted by a "halogen" group.

"Haloaryl" refers to an "aryl" group substituted with from one to four halogen groups.

"Optional" or "optionally" means that the subsequently described event or circumstance may or may not occur, and that the description includes instances where said event or circumstance occurs and instances in which it does not. For example, "optionally substituted phenyl" means that the phenyl may or may not be substituted, and that the description includes both unsubstituted phenyl and phenyl wherein there is substitution.

In describing the location of groups and substituents, the following numbering system will be employed.

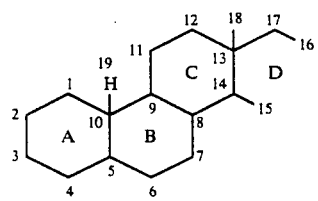

This system is intended to conform the numbering of the cyclopentanophenanthrene nucleus to the convention used by the IUPAC or Chemical Abstracts Service.

In these structures, the use of bold and dashed lines to denote particular conformation of groups again follows the IUPAC steroid-naming convention. (The symbols "α" and "β" indicate the specific stereochemical configuration of a substituent at an asymmetric carbon atom in a chemical structure as drawn. Thus "α", denoted by a broken line, indicates that the group at the position in question is below the general plane of the molecule as drawn, and "β", denoted by a bold line, indicates that the group at the position in question is above the general plane of the molecule as drawn.)

In addition, the five- or six-membered rings of the steroid molecule are often designated A, B, C and D as shown.

THE NOVEL COMPOUNDS

The novel compounds provided herein are those defined by the structural formulae (Ia), (Ib), (II), (IIIa), (IIIb), (IV), (Va), (Vb), (VI), (VII), and (VIII) above. Each of the novel compounds is "15,16-seco" in that the D-ring of the cyclopentanophenanthrene nucleus is open at those positions, i.e., there is no bond between the C-15 and the C-16 positions. The compounds are also designated "19-nor" herein to indicate that a hydrogen atom rather than a carbon-containing substituent is present at 19-position. The preferred compounds within these groups are as follows.

In the groups of compounds defined by formulae (Ia) and (Ib), preferred compounds are wherein R is hydrogen or an acyl group of the formula —(C=O)—Y, Y is selected from the group consisting of lower alkyl, cycloalkyl, phenyl optionally substituted with 1 or 2 lower alkyl, lower alkoxy, hydroxy and/or nitro substituents, and five- and six-membered heterocyclic rings, R' is hydrogen, R" is hydrogen, and $R^1$ is hydrogen or lower alkynyl. Particularly preferred compounds of formulae (Ia) and (Ib) are wherein R is —(C=O)—Y, Y is selected from the group consisting of methyl, cyclobutyl, 3,5-dinitrophenyl, and furanyl, $R^1$ is hydrogen or —C≡CH, $R^2$ is hydrogen, methyl or cyano, and A represents a double bond. An exemplary compound within the class defined by formula (Ia) is 17β-acetoxy-7α-methyl-15,16-seco-19-norandrosta-4-en-3-one.

Within the class of compounds encompassed by formula (II), preferred compounds are those wherein R' is hydrogen, R" is hydrogen, $R^2$ is hydrogen, methyl, or cyano, and A represents a double bond.

With regard to formulae (IIIa) and (IIIb), preferred compounds that fall within the purview of these structures are those wherein R is hydrogen or an acyl group of the formula —(C=O)—Y, Y is selected from the group consisting of lower alkyl, cycloalkyl, phenyl optionally substituted with 1 or 2 lower alkyl, lower alkoxy, hydroxy and/or nitro substituents, and five-and six-membered heterocyclic rings, and $R^1$ is hydrogen or lower alkynyl. As with the compounds of formulae (Ia) and (Ib), particularly preferred compounds of formulae (IIIa) and (IIIb) are wherein R is —(C=O)—Y, Y is selected from the group consisting of methyl, cyclobutyl, 3,5-dinitrophenyl, and furanyl, $R^1$ is hydrogen or —C≡CH, $R^2$ is hydrogen, methyl or cyano, and B represents a double bond.

Within the class of compounds encompassed by formula (IV), preferred compounds are those wherein $R^2$ is hydrogen, methyl, or cyano, and B represents a double bond.

With regard to compounds defined by formulae (Va) and (Vb), preferred compounds are those wherein R is hydrogen or an acyl group of the formula —(C=O)—Y, Y is selected from the group consisting of lower alkyl, cycloalkyl, phenyl optionally substituted with 1 or 2 lower alkyl, lower alkoxy, hydroxy and/or nitro substituents, and five- and six-membered heterocyclic rings, and $R^1$ is hydrogen or lower alkynyl. As with the compounds of formulae (Ia), (Ib), (IIIa) and (IIIb), particularly preferred compounds of formulae (Va) and (Vb) are wherein R is —(C=O)—Y, Y is selected from the group consisting of methyl, cyclobutyl, 3,5-dinitrophenyl, and furanyl, $R^1$ is hydrogen or —C≡CH, and $R^2$ is methyl or cyano.

Preferred compounds defined by formula (VI) are wherein $R^2$ is hydrogen, methyl or cyano.

Preferred compounds defined by formula (VII) are wherein $R^2$ is hydrogen or methyl, more preferably hydrogen, while preferred compounds within the scope of formula (VIII) are wherein R' and R" are hydrogen.

Process for Preparation

The compounds of the invention may be prepared in high yield using relatively simple, straightforward methods as exemplified in the experimental section herein.

Synthesis of representative compounds of formulae Ia and Ib is described, inter alia, in Examples 1, 2, 3 and 5 below. As illustrated in Schemes and 2 below, a 1,3,5(10)-triene-17-one is generally used as the starting material, working through 17-hydroxyl intermediates to obtain the desired product. Preparation of a III-type compound, i.e., a 3β,17β-dihydroxy material, is described exemplified in Example 4, and involves synthesis from a 17β-acetoxy-3-one. Compounds of formula II may be prepared by conversion of the 17-hydroxy moiety to a 17-one as described in Example 7 (Scheme 6). The 1,3,5(10)-trienes of V and VI may be derived as illustrated in Scheme 1.

The method of synthesizing a compound of formula

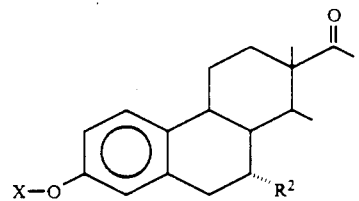

which comprises reacting a starting material of formula

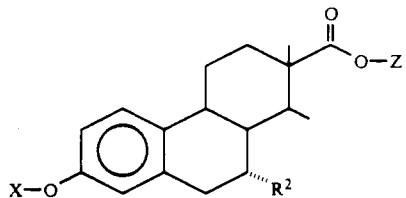

with methylmagnesium bromidein the presence of a lower alkyl amine is considered to be novel and represents an aspect of the present invention. In the above formulae, X is a hydroxyl protecting group, preferably an aromatic species such as benzyl, Z is lower alkyl, e.g., methyl and $R^2$ is hydrogen, lower alkyl, or cyano. In a preferred embodiment, the lower alkyl amine is triethyl amine. This reaction is exemplified in section (a.) of Example 1.

Utility and Administration

The compounds disclosed and claimed herein are useful for achieving therapeutic or prophylactic progestational effects in a patient. As noted above, progestins, including the present compounds, are useful for the following purposes: suppressing ovulation in the human female; controlling uterine bleeding; treating amenorrhea and dysmenorrhea; alleviating endocrine disorders; in conjunction with chemotherapy; and in treating infertility.

In the preferred embodiment, the present compounds are used either alone or in combination with one or more estrogenic components in a contraceptive composition, within the context of a dosing regimen effective to suppress ovulation. A number of such dosing regimens have been developed and are well-known in the art. So-called monophasic dosing regimens involve a constant daily dose of a progestin and an estrogen for 21 days of the menstrual cycle, while a biphasic regimen involves two 10/11 day dosing periods in which a lower dose of progestogen is administered throughout the first period, followed by administration of a higher dose throughout the second period. The currently popular triphasic regimen involves stepped-up administration of the progestogen component throughout the three phases of the cycle, with a higher dose of estrogen administered in the middle phase. A sequential, nonphasic regimen is also known; in such a regimen, the progestogen is only administered for five days at the end of the cycle. Relative quantities of estrogen and progestogen in these compositions vary. Typically, "combination" pills contain from about 25–50 micrograms estrogen and 0.3 to 3.0 mg progestin.

Suitable estrogens useful in contraceptive compositions containing the present progestins include estradiol and its esters, e.g., estradiol valerate, cypionate, decanoate and acetate, as well as ethinyl estradiol. The progestin may also be administered without an estrogenic component for purposes of suppressing ovulation in a human female.

Administration of the active compounds described herein can be via any of the accepted modes of administration of therapeutic agents. These methods include parenteral, transdermal, subcutaneous and other systemic modes. For those compounds herein which are orally active, oral administration is the preferred mode. For those compounds which are not orally active, administration in the form of a long-acting injectable composition is preferred.

Depending on the intended mode of administration, the compositions may be in the form of solid, semi-solid or liquid dosage forms, such as, for example, tablets, suppositories, pills, capsules, powders, liquids, suspensions, or the like, preferably in unit dosage forms. suitable for single administration of precise dosages. The compositions will include a conventional pharmaceutical excipient and one or more of the present progestins or pharmaceutically acceptable salts thereof and, in addition, may include other medicinal agents, pharmaceutical agents, carriers, adjuvants, diluents, etc.

The amount of active compound administered will, of course, be dependent on the subject being treated, the subject's weight, the manner of administration and the judgment of the prescribing physician. However, an effective dosage amount for purposes of suppressing ovulation is generally in the range of about 0.2–20 mg/kg/day.

For solid compositions, conventional nontoxic solids include, for example, pharmaceutical grades of mannitol, lactose, starch, magnesium stearate, sodium saccharin, talc, cellulose, glucose, sucrose, magnesium carbonate, and the like may be used. The active compound as defined above maybe formulated as suppositories using, for example, polyalkylene-glycols, for example, propylene glycol, as the carrier. Liquid pharmaceutically administrable compositions can, for example, be prepared by dissolving, dispersing, etc. an active compound as defined above and optional pharmaceutical adjuvants in an excipient, such as, for example, water, saline, aqueous dextrose, glycerol, ethanol, and the like, to thereby form a solution or suspension. If desired, the pharmaceutical composition to be administered may also contain minor amounts of nontoxic auxiliary substances such as wetting or emulsifying agents, pH buffering agents and the like, for example, sodium acetate, sorbitan monolaurate, triethanolamine sodium acetate, triethanolamine oleate, etc. Actual method of preparing such dosage forms are known, or will be apparent, to those skilled in this art; for example, see *Remington's Pharmaceutical Sciences*, Mack. Publishing Company, Easton, Penn., 15th Edition, 1975. The composition or formulation to be administered will, in any event, for purposes of suppressing ovulation, contain a fertility-controlling amount of the desired progestin(s), i.e., an amount effective to achieve the desired fertility control in the female subject being treated.

For oral administration, i.e., of any of the present compounds which may be orally active, a pharmaceutically acceptable nontoxic composition is formed by the incorporation of any of the normally employed excipients described above. Such compositions take the form of solutions, suspensions, tablets, pills, capsules, powders, sustained-release formulations and the like. Such compositions may contain 1%–95% active ingredient, preferably 1–10%, and will preferably contain an estrogenic component as noted above.

Parenteral administration, if used, is generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol or the like. In addition, if desired, the pharmaceutical compositions to be administered may also contain minor amounts of nontoxic auxiliary substances such a wetting or emulsifying agents, pH buffering agents and the like, such as, for example, sodium acetate, sorbitan monolaurate, triethanolamine oleate, etc.

A more recently revised approach for parenteral administration employs the implantation of a slow-release or sustained-release system, such that a constant level of dosage is maintained. See, e.g., U.S. Pat. No. 3,710,795, which is incorporated herein by reference.

It is to be understood that while the invention has been described in conjunction with the preferred specific embodiments thereof, that the foregoing description as well as the examples which follow are intended to illustrate and not limit the scope of the invention. Other aspects, advantages and modifications within the scope of the invention will be apparent to those skilled in the art to which the invention pertains.

EXAMPLES
The following Examples 1 through 17 illustrate sequentially the synthesis of various compounds of the invention.
EXAMPLE 1
This example describes the preparation of 17β-acetoxy-7α-methyl-15,16-seco-19-norandrosta-4-en-3-one (12) as outlined in Scheme 1.
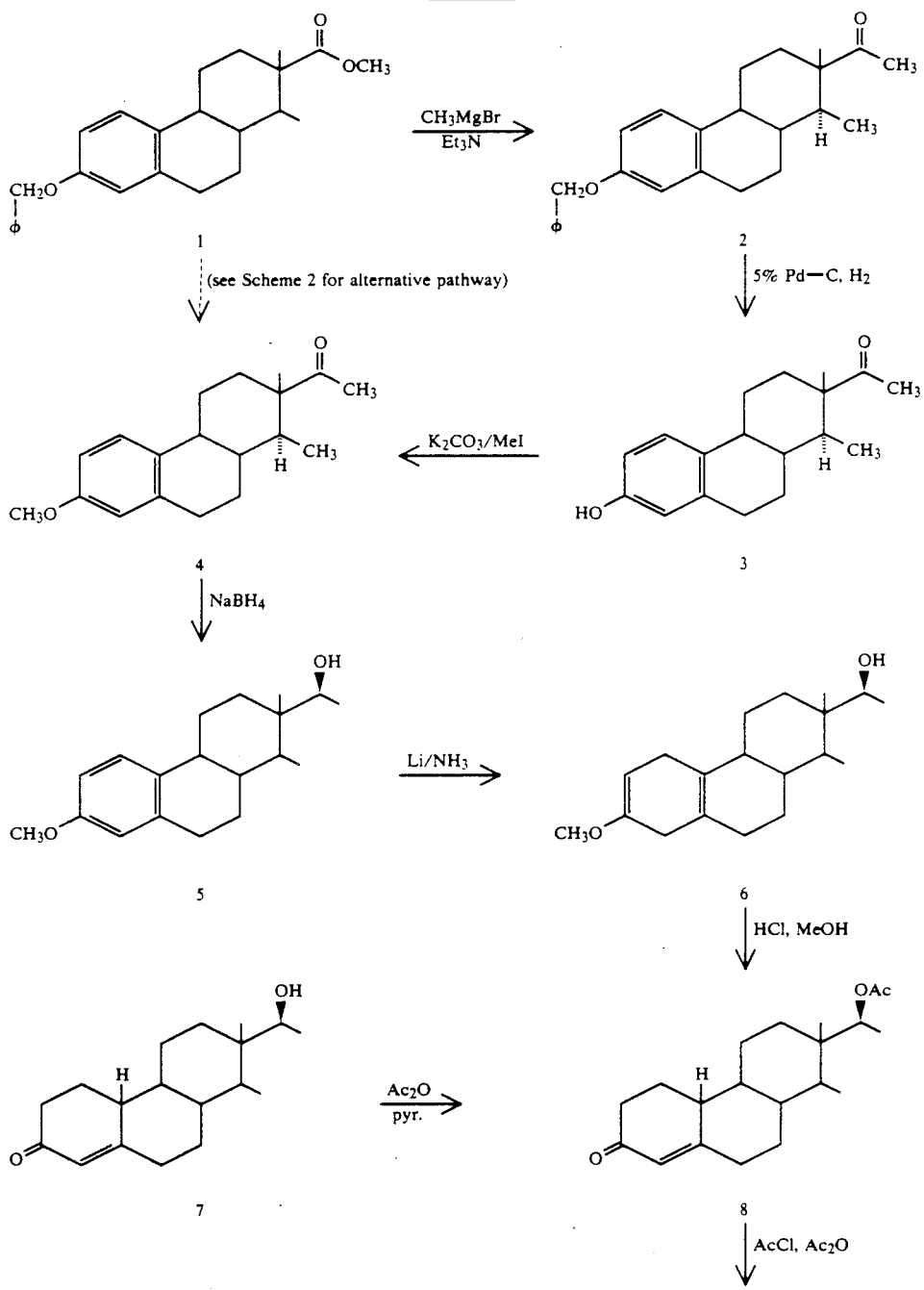
Scheme 1

Scheme 1 -continued

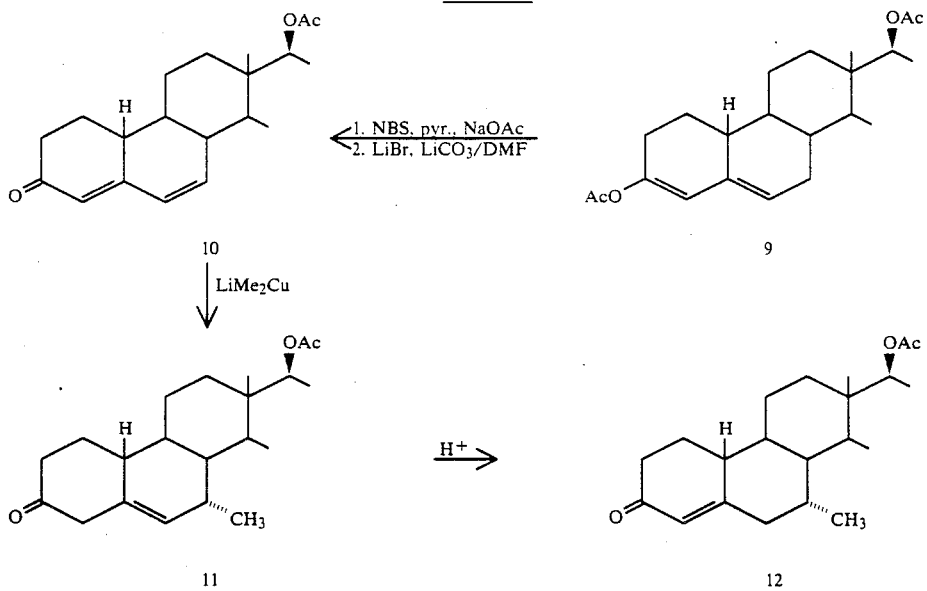

(a.) Synthesis of 3-Benzyloxy-16,17-seco-16-norestra-1,3,5(10)-trien-17-oic Acid Methyl Ester (1):

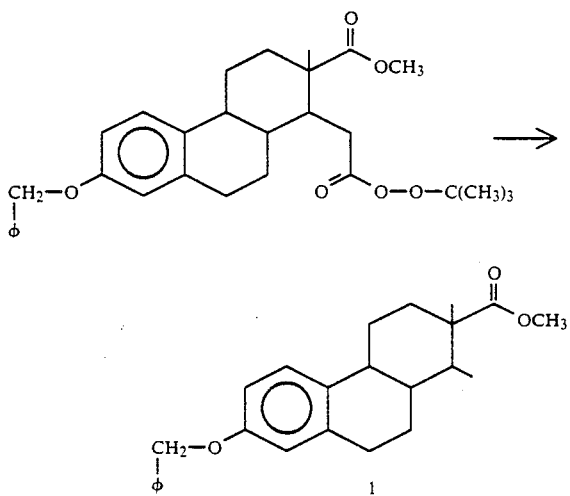

A solution of 7.6 g of 3-benzyloxy-16,17-secoestra-1,3,5(10)-triene-16,17-dioic 16-t-butyl perester 17-methyl ester in 300 ml of freshly distilled cumene was purged with nitrogen for 1 hr. The cumene solution was then refluxed for 1 hr and the solvent removed in vacuo to yield 7.7 g of a semi-solid residue. Chromatography of 7.5 g of this residue on 500 g of silica gel and elution with benzene afforded 4.4 g of pure 1. Recrystallization from methanol afforded an analytical sample, mp 97°-99° C., lit mp 96°-98° C. (M. A. Bierefeld and R. Oslapas, J. Med. Chem. 12, 192, 1969).

(b.) Synthesis of 3-Benzyloxy-15,16-secoestra-1,3,5,(10)-triene-17-one (2):

To a solution of 13.5 of 1 in 800 ml of dry THF (distilled from methylmagnesium bromide) was added 8.3 ml of dry triethylamine. (Dry triethylamine was prepared by passing it through a column of Woelm alumina activity grade super I.) To the THF solution was added dropwise 82 ml of 2.9M methylmagnesium bromide in ether. The reaction was allowed to stir at room temperature for 4 hr. TLC indicated ester (2) remained, so an additional 41 ml of 2.9M methylmagnesium bromide was added. The reaction was stirred for an additional 18 hr at room temperature, then poured slowly into 4% hydrochloric acid, and extracted with ether. The ether solution was separated and washed with 4% hydrochloric acid, 4% sodium hydroxide, and water. The ether solution was dried over sodium sulfate and evaporated at reduced pressure to yield 14.1 g of product 2, which was purified by thick-plate chromatography.

Anal. High-Resolution Mass Spec. for $C_{25}H_{30}O_2$: Calcd.: 362.2246; found: 362.2233. NMR and IR spectra were consistent with the assigned structures.

(c.) Synthesis of 3-Hydroxy-15,16-secoestra-1,3,5,(10)-triene-17-one (3):

To a solution of 14.1 g of in 800 ml of absolute ethanol was added 1.0 g of 5% palladium on carbon. The suspension was hydrogenated at room temperature and at atmospheric pressure for 18 hr. The suspension was filtered through celite to remove the palladium on carbon catalyst. The ethanol was evaporated at reduced pressure to yield 3. Recrystallization from methanol afforded 8.1 g of an analytical sample of 3; mp 181.5° C.

Anal. calcd. for $C_{18}H_{24}O_2$: C, 79.37; H, 8.88. Found: C, 79.37; H, 8.93.

(d.) Synthesis of 3-Methoxy-15,16-secoestra-1,3,5,(10)-triene-17-one (4):

To a solution of 6.5 g of 3 in 600 ml of acetone was added 12.6 g of potassium carbonate and 2.1 ml of methyl iodide. The reaction was allowed to stir at room temperature for 48 hr. Approximately half of the volume of acetone was evaporated at reduced pressure. The remaining suspension was poured into water and extracted with ether. The ether solution was washed with water, dried over sodium sulfate, and evaporated at reduced pressure to yield 6.2 g of Recrystallization from methanol afforded an analytical sample of 4; mp 64° C.

Anal. calcd. for $C_{19}H_{26}O_2$: C, 79.68; H, 9.15. Found: C, 79.26; H, 9.16.

(e.) Synthesis of 3-Methoxy-17β-hydroxy-15,16-secoestra-1,3,5(10)-triene (5):

To a solution of 25.0 g of 3-methoxy-15,16-secoestra-1,3,5(10)-triene-17-one (4) in 1.0 L of methanol at 0°–5° (ice bath) was added portion-wise 6.61 g of sodium borohydride. The reaction mixture was stirred at 0°–5° for 1.8 hr and then quenched with the slow addition of 1.5 ml of acetic acid. The reaction mixture was poured into 3.0 L of water. The milky suspension was extracted with ether. The ether solution was washed with water, dried over sodium sulfate and evaporated at reduced pressure to afford 24.8 g of 5. The crude product, when analyzed by NMR and thin-layer chromatography (TCL)-25% tetrahydrofuran/hexane—indicated the presence of two C-17 isomers—the major product being 5. An analytical sample of 5 was obtained by recrystallization from acetone/hexane, mp 84°–85° C.

Anal. Calcd. for $C_{19}H_{28}O_2$: C, 79.12; H, 9.78. Found: C, 79.31; H, 9.66.

(f.) Synthesis of 3-Methoxy-17β-hydroxy-15,16-secoestra-2,5(10)-diene (6):

To a solution of 2.0 L of ammonia at −78° C. (dry ice-acetone) was added 12.04 g of lithium wire washed with hexane. After 1.0 hr, 24.9 g of (5) in a mixture of 300 ml of ether and 100 ml of absolute ethanol was added to the dark blue ammonia lithium solution at −78° C. The reaction was stirred at −78° C. for an additional 2 hr while the dark blue color remained. The reaction was quenched with the slow addition of 200 ml of ethanol. The reaction was allowed to warm to room temperature, and the ammonia was evaporated over 18 hr. The white solid residue was dissolved in ether and water. The organic phase was separated and washed with water, dried over sodium sulfate, and evaporated at reduced pressure to yield 24.8 g of product 6.

(g.) Synthesis of 17β-Hydroxy-15,16-seco-19-norandrosta-4-en-3-one (7):

To a suspension of 24.8 g of 6 in 500 ml of methanol was added dropwise 1.0 ml of concentrated hydrochloric acid. The reaction was stirred at room temperature for 18 hr. The methanol was evaporated to half its volume at reduced pressure and then poured into water. The milky suspension was extracted with ether, and the ether solution was washed with water, dried over sodium sulfate, and evaporated to dryness at reduced pressure to afford 26.2 g of crude product 7. The crude product 7 was recrystallized from ether to yield pure 7 mp 155°–156° C.

Anal. High Res. Mass Specs for $C_{18}H_{28}O_2$: Calcd., 276.2089; found, 276.2086.

Anal. Calcd. for $C_{18}H_{28}O_2$; C, 78.21; H, 10.21. Found: C, 78.33; H, 10.00.

(h.) Synthesis of 17β-Acetoxy-15,16-seco-19-norandrosta-4-en-3-one (8):

A solution of 10.0 g of 7 in 30 ml of pyridine and 10.0 ml of acetic anhydride was stirred at room temperature for 18 hr. The reaction mixture was poured into ether/water and the organic phase was separated. The aqueous phase was extracted several times with ether. The ether solutions were combined, washed with water, 4% hydrochloric acid, and water. The ether solution was dried over sodium sulfate and evaporated at reduced pressure to yield 11.42 g of 8. An analytical sample was obtained by recrystallization from methanol, mp 143°–145° C.

Anal. High Res. Mass Spec. for compound 8 $C_{20}H_{30}O_3$: Calcd., 318.2195; found, 318.270.

Anal. Calcd. for $C_{20}H_{30}O_3$: C, 75.43; H, 9.50. Found: C, 75.14; H, 9.33.

(i.) Synthesis of 3.17β-diacetoxy-15,16-seco-19-norandrosta-3,5-diene (9):

A solution of 11.32 g of 8 in 5.0 ml of acetic anhydride containing 80.0 ml of freshly distilled acetyl chloride was refluxed for 4.0 hr. The solvent was removed at reduced pressure and the resulting oil was triturated with cold aqueous sodium bicarbonate and ice-water. The trituration, at first, gave an oil that on standing, afforded a white crystalline solid, which was filtered and air-dried to afford 11.7 g of 9. An analytical sample was obtained by recrystallizing 9 from acetone, mp 164°–167° C.

Anal. High Res. Mass Spec. for compound $C_{22}H_{32}O_4$: Calcd., 360.2300; found, 360.2311.

(j.) Synthesis of 17β-Acetoxy-15,16-seco-19-norandrosta-4,6-dien-3-one (10):

To a solution of 10.78 g of 9 in 650.0 ml of acetone and 120.0 ml water containing 76.5 ml acteic acid, 6.4 ml pyridine, and 14.07 g of sodium acetate at 0°–5° C. (ice-water bath) was added 5.83 g of recrystallized N-bromosuccinimide. The N-bromosuccinimide had been previously recrystallized from water and dried under vacuum over conc. sulfuric acid for five days. The reaction was stirred at 0°–5° C. for 3 hr while the flask was totally shielded from light. The reaction mixture was poured into cold saturated sodium chloride and extracted with ether. The ether solution was washed with saturated sodium chloride, dried over sodium sulfate, and evaporated at reduced pressure to afford 76.4 g of bromoenone. The bromoenone was used immediately without purification in the subsequent dehydrobromination reaction. The bromoenone (16.4 g) was dissolved in 200.0 ml of dimethylformamide and added to a boiling suspension of 10.2 g of lithium bromide and 10.2 g of lithium carbonate in 400.0 ml of dimethylformamide. The suspension was refluxed for 1.0 hr and then cooled. The suspension was filtered, the filtrate was poured into an ice-water solution, and the mixture was extracted with ether. The ether solution was washed with 4% sodium hydroxide, water and saturated sodium chloride. The ether solution was dried over sodium sulfate and evaporated at reduced pressure to yield 10.2 g of 10. An analytical sample was obtained by recrystallization from methanol, mp 162°–163° C.

Anal. High Res. Mass Spec. for compound $C_{20}H_{28}O_3$: Calcd., 316.2058; found, 316.2038.

(k.) Synthesis of 17β-Acetoxy-7α-methyl-15,16-seco-19-norandrosta-5-en-3-one (11):

To a suspension of 11.82 g of copper (I) iodide in 360.0 ml of anhydrous ether at 0°–5° C. (ice-water bath) was added, via a syringe, 82.6 ml of 1.55M methyllithium in ether. The resulting dark brown-grey solution was stirred at 0°–5° C. for 15 min. A solution of 4.0 g of 17β-acetoxy-15,16-seco-19-norandrosta-4,6-dien-3-one in 120.0 ml of dry tetrahydrofuran (distilled from methylmagnesium bromide) was added dropwise (25 min) to the reaction mixture. The reaction mixture was stirred for an additional 0.5 hr at 0–5° C. and then poured into cold aqueous saturated ammonium chloride, with vigorous stirring. Approximately 1.0 L of benzene was added and stirring was continued for 0.5 hr. The organic layer was separated and washed with additional ammonium chloride. The benzene solution was separated and dried over magnesium sulfate and evaporated to dryness at reduced pressure, to afford 4.1 g of crude product. A portion of the residue was purified by thick-plate chromatography on silica gel plate and developed with 25% tetrahydrofuran in hexane to afford pure 11.

Mass Spec. for compound 11, $C_{21}H_{32}O_3$: Calcd., 332; found, 332.

(1.) Synthesis of 17β-Acetoxy-7α-methyl -15,16-seco-19-norandrosta-4-en-3-one (12):

A solution of crude 11 was dissolved in 500 ml of benzene containing a catalytic amount of PTSA. The solution was heated on a steam bath for 0.5 hr. The reaction was cooled to room temperature and then poured into water. The organic layer was separated and washed with water, dried over magnesium sulfate, and evaporated at reduced pressure to afford 1.2 g of crude product. The crude product was purified by HPLC using 12% ethyl acetate/hexane as the eluant to afford pure An. analytical sample was obtained by recrystallization from hexane, mp 105°–106° C.

Anal. Calcd. for $C_{21}H_{32}O_3$; C, 75.86; H, 9.70. Found: C, 75.78; H, 9.34.

EXAMPLE 2

This example describes an alternative pathway to 3-methoxy-15,16-secoestra-1,3,5,(10)-triene-17-one (4) as illustrated in Scheme 2.

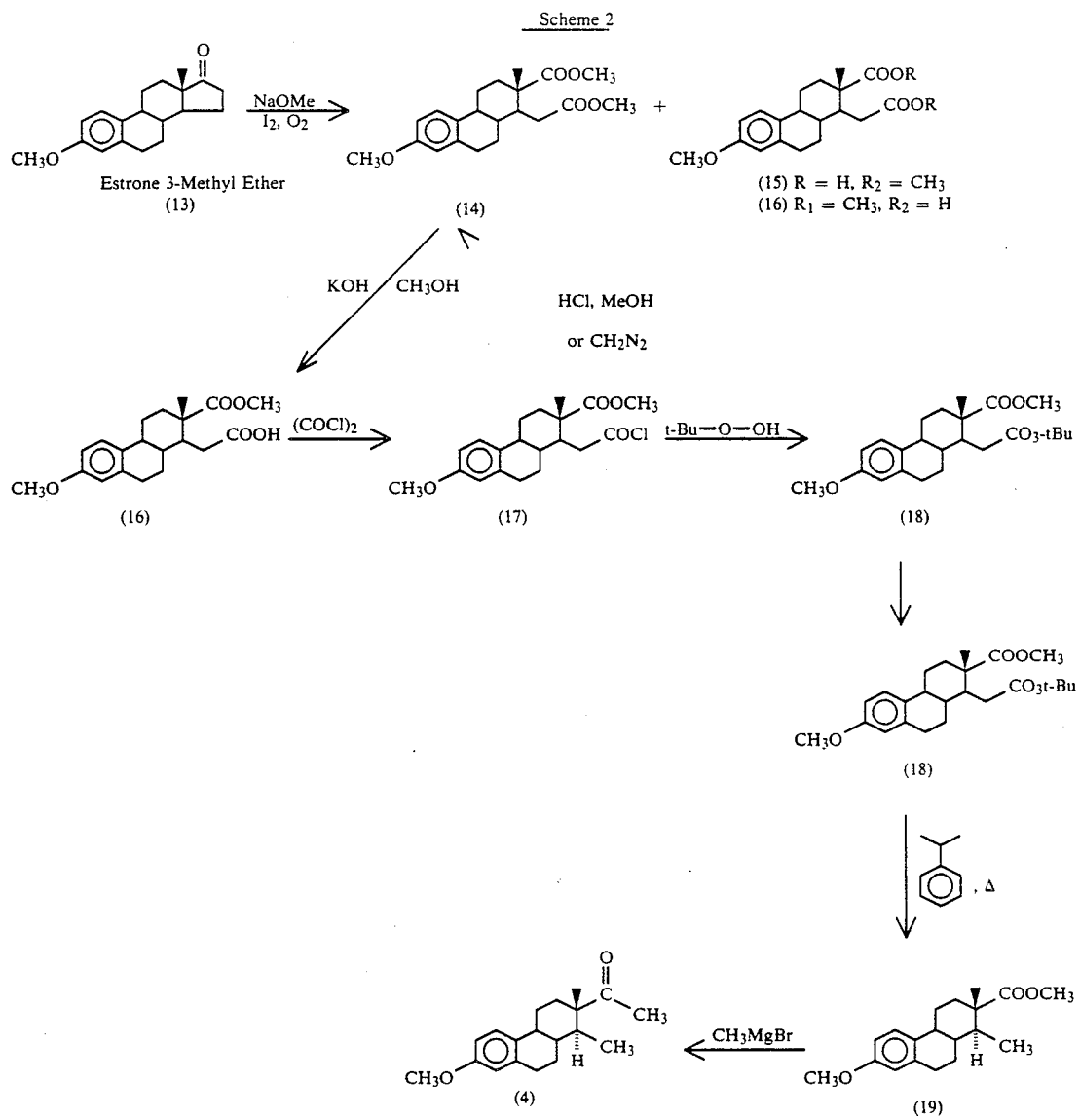

Oxidative cleavage of ring D of 3-methylestrone (13) with sodium methoxide and iodine under aeration yielded the diester 14 and a mixture of monoacids 15 and 16. The mixture of acids was esterified in methanol containing sulfuric acid to complete the conversion to diester 14 in an overall combined yield of 95%. Selective saponification of 14 with methanolic KOH gave the crude monoester 16. Treatment of 16 with an excess of oxalyl chloride in benzene afforded the crude acid chloride 17. Treatment of 17 with t-butyl hydroperoxide in benzene with pyridine furnished the perester 18 in good yield. Decomposition of the perester in boiling cumene gave the decarboxylated product 19. Attempts to synthesize the methyl ketone 4 via Corey's protocol were thwarted: addition of methylsulfinyl carbanion to the methyl ester 19 followed by reductive cleavage of the resulting β-keto sulfoxide with aluminum amalgam were unsuccessful. Therefore, for the conversion of ester 19 to the methyl ketone Kikkawa's observation (I. Kikkawa et al., Synthesis 11:877 (1980)) that Grignard reagents react with esters in the presence of a tertiary amine to give alkyl ketone without overreaction to alcohols was utilized. By this method, 4 was obtained in high yield by treating the methyl ester 19 with an excess of an equimolar admixture of methylmagnesium bromide and triethylamine, as follows.

To an anhydrous solution of the ester (19, 50 g) and triethylamine (45 ml) in tetrahydrofuran (500 ml) under nitrogen, was added dropwise a solution of methyl magnesium bromide in ether (1.0 mole). (Dry triethylamine was prepared by passing it through a column of Woelm alumina, activity grade Super I.) The reaction mixture was stirred at ambient temperature, under nitrogen, overnight, and then poured cautiously into a mixture of concentrated hydrochloric acid (50 ml) and crushed ice (~1000 ml). Ice and concentrated hydrochloric acid were added until the mixture was ~pH 4 and the magnesium salts were dissolved The aqueous and tetrahydrofuran layers were separated and the tetrahydrofuran was evaporated in vacuo. The residue was taken into ether, washed successively with water, saturated sodium bicarbonate solution, water, and brine, dried over $Na_2SO_4$, and filtered. Evaporation of solvent gave the crude methyl ketone (4, 44.8 g). The pure ketone was obtained by dissolving the residue in methanol and then cooling it in a dry ice-isopropanol bath. The methanol was then decanted and the residue was again dissolved in methanol. The methyl ketone (4) crystallized in both the decantate (4.6 g) and the residue (25.9 g). The residue was crystallized once again to give the pure methyl ketone (16.1 g, mp 63.5°-65° C). The residue was purified by preparative liquid chromatography PrepPak column, hexanes:ethyl acetate, 95:5, 200 ml/min). After in vacuo evaporation of the chromatography solvent, the residue was crystallized from methanol to give the pure ketone (4, 7.8 g, 28.7 g total for the reaction).

EXAMPLE 3

This example describes a procedure analogous to the reaction set forth in Example 1, part (a), but involves the preparation of a compound having a methoxy group at the 3-position rather than a benzyloxy group.

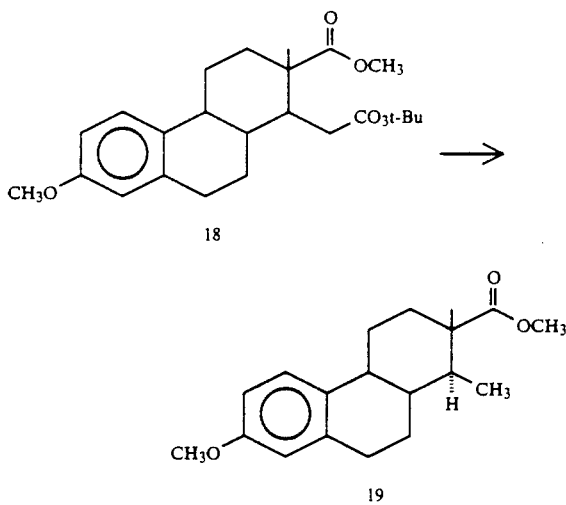

3-Methoxy-16,17-secoestra-1,3,5(10)-trien -17-oic acid methyl ester (19): A solution of 83.1 g of 3-methoxy-16,17-secoestra-1,3,5(10)-triene -16,17-dioic16-t-butyl perester 17-methyl ester (18) (obtained by the method of M.A. Bierefeld and R. Oslapas, supra, in freshly distilled cumene was purged with nitrogen for 1 hr, then refluxed for 1 hr. The cumene was removed under reduced pressure to give 83.1 g of a semi-solid residue. The residue was triturated with methanol and filtered to remove 14.7 g of dicumene as a white crystalline solid. The remaining material containing the ester was purified by preparative liquid chromatography PrepPak column, hexane:ethyl acetate, 95:5, 20 ml/min). Three fractions were collected containing: (i) dicumene (7.6 g); (ii) the desired ester (49.6 g); and (iii) a slightly more polar product later established by NMR to be the tert-butyl ether (4.5 g). Evaporation of chromatography solvents yielded the ester as a white solid which was used without further purification. A total of 129.8 g of the ester was obtained (54% yield). An analytical sample was obtained by recrystallization from methanol to give the pure ester 19, mp 55°-57° C.

Anal. Calcd. for $C_{19}H_{26}O_3$: C, 75.46; H, 8.67. Found: C, 75.77; H, 8.64.

EXAMPLE 4

This example illustrates the preparation of 3β,17β-dihydroxy-7α-methyl-15,16-seco-19-norandrosta-5-en-3β-ol (22) according to Scheme 3:

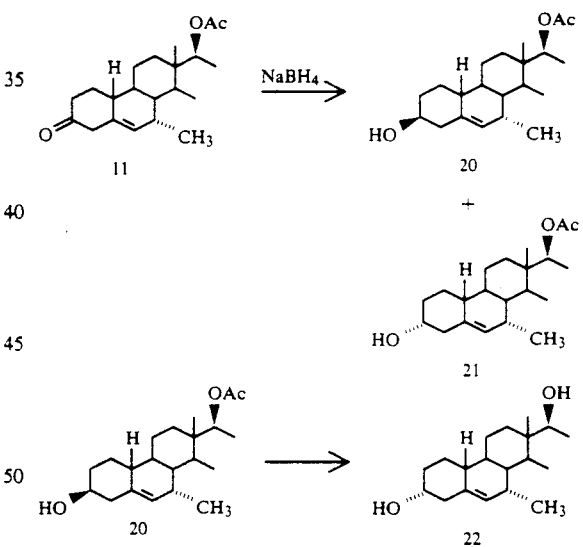

(a.) 17β-Acetoxy-7β-methyl-15,16-seco-19-norandrosta-5-en-3β-ol (20) and 17β-acetoxy-7α-methyl-15,16-seco-19-norandrosta-5-en-3α-ol (21): To a solution of 1.80 g of 11 in 180 ml of methanol at 0°-5° C. (ice-water bath) was added 1.80 g of sodium borohydride in 0.200 g portions. The reaction was stirred at 0°-5° C. for 20 min, then poured into ice water and extracted with ether. The ether solution was washed with saturated sodium chloride, dried over magnesium sulfate, and evaporated at reduced pressure to afford 1.92 g of a mixture of 20 and 21. The mixture was separated on a Waters preparative HPLC silica gel column, using 15% ethyl acetate/hexane as the solvent to afford 0.413 g of pure and 0.250 g of pure as glasses.

Anal. Hi. Res. Mass Spec. for compound 20, $C_{12}H_{34}O_3$: Calcd., 334.2476; found, 334.2508. For compound 21: Calcd., 334.2476; found, 334.2510.

(b.) 3β,17β-Dihydroxy-7α-methyl-15,16-seco-19-norandrosta-5-en-3β-ol (22): A suspension of 0.413 g of 20 in 100 ml of 10% potassium hydroxide in methanol was stirred at room temperature for 18 hr. The reaction was poured into water and extracted with ether. The ether solution was washed with water, dried over magnesium sulfate, and evaporated at reduced pressure to afford 0.30 g of 22. Purification by chromatography on preparative thick plate developed in 25% tetrahydrofuran/hexane and recrystallization from acetone afforded pure 22; mp 186°-187° C.

Anal. Hi. Res. Mass Spec. for compound $C_{19}H_{32}O_2$: Calcd., 292.2402; found, 292.2386.

EXAMPLE 5

This example describes the synthesis of 17β-acetoxy-7α-cyano-15,16-seco-19-norandrosta-4-en-3-one(23) as illustrated by Reaction Scheme 4:

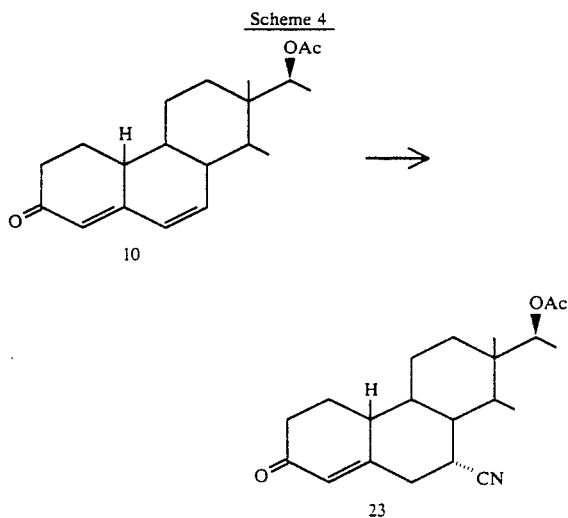

17β-Acetoxy-7α-cyano-15,16-seco-19-norandrosta-4-en-3-one (23): To a solution of 0.26 g of 10 in 11 ml of dry THF (dried by distillation from methylmagnesium bromide and storage over molecular sieves (Aldrich 4Å)) under argon was added 2.4 ml of a 1.8M solution of diethylaluminum cyanide (in toluene). The mixture was stirred at room temperature under argon for 1 hr and then added to a 2N sodium hydroxide solution. The cloudy solution was extracted with ether. The combined ether extract was washed with 2N sodium hydroxide solution and water and then dried over sodium sulfate. The ether solution was evaporated to dryness at reduced pressure. The residue (0.263 g) was chromatographed on a Waters 500 preparative HPLC equipped with a 1-inch-diameter stainless steel column. The product was eluted with 5% ethyl acetate/chloroform. This procedure afforded 0.112 g of pure 23. Trituration with ether gave an analytical sample, mp 194°-196° C.

Anal. Calcd. for compound 23, $C_{21}H_{29}NO_3$: Calcd.: C, 73.44; H, 8.51; N, 4.08. Found: C, 73.19; H, 8.50; N, 4.03.

EXAMPLE 6

This example describes the preparation of 17β-acetoxy-7α-methyl-15,16-seco-19-nor-5α-androsta-3-one(24) according to Scheme 5:

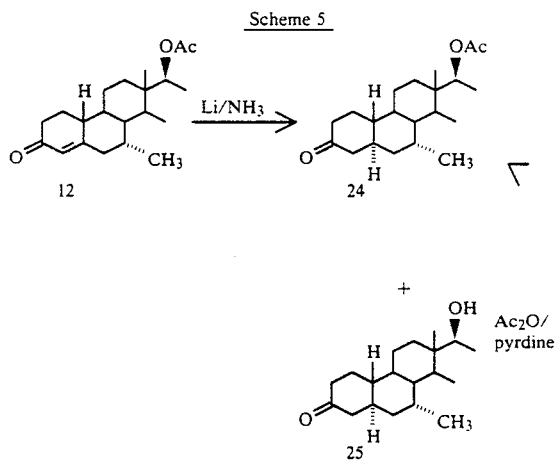

To 100 ml of ammonia at −78° C. (dry ice-acetone) was added 0.076 g of lithium wire washed with hexane. After 1.0 hr. 0.352 g of 12 in 30 ml of dry THF (distilled from methylmagnesium bromide and stored over molecular sieves, Aldrich 4Å) was added to the dark blue ammonialithium solution at −78° C. The reaction was stirred at −78° C. for 2 hr while the dark blue color remained. The reaction was then quenched by the slow addition of 5 ml of 1,2-dibromoethane. After the color of the reaction mixture had turned to white, the cooling bath was removed and the ammonia was allowed to evaporate overnight. The residue was dissolved in ether/water. The ether solution was washed with water several times, dried over magnesium sulfate, and evaporated to dryness at reduced pressure to yield 0.401 g of a mixture. NMR analysis indicated that the mixture had C-17 hydroxy (25) and C-17 acetoxy (24) functionalities.

The reaction mixture (0.401 g) was dissolved in 1.0 ml of pyridine containing 1.0 ml of acetic anhydride. The solution was stirred at room temperature for 18 hr and then poured into water and extracted with ether. The ether solution was washed with water, 4% hydrochloric acid, and water. The ether solution was then dried over magnesium sulfate and evaporated to dryness at reduced pressure to yield 0.409 g of crude product 24. Chromatography of crude product 24 on preparative HPLC, using a 1-in. stainless steel column packed with normal-phase silica gel and eluting with 10% ethyl acetate/petroleum ether (bp 35°-60° C.), afforded 0.140 g of an analytical sample of 17β-acetoxy-7α-methyl-15,16-seco-19-nor -5α-androsta-3-one 24; mp 121°-122° C.

Anal. Hi. Res. Mass Spec. for compound $C_{21}H_{34}O_3$: Calcd. ($C_{19}H_{30}O$, M-HOAc), 274.2297; found, 274.3316. Also Calcd. ($C_{17}H_{27}O$, M-$C_4H_7O_2$), 247.2075; found, 247.2062.

Mass Spec. using chemical ionization mass spectrum analysis for $C_{21}H_{34}O_3$: Calcd. 334; Found, 334.

EXAMPLE 7

This example sets forth the synthesis of 15,16-seco-5α-19-norandrosta-3,17-dione (27) according to Scheme 6:

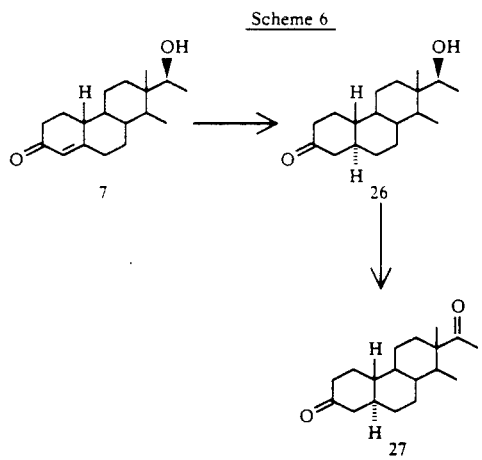

Scheme 6

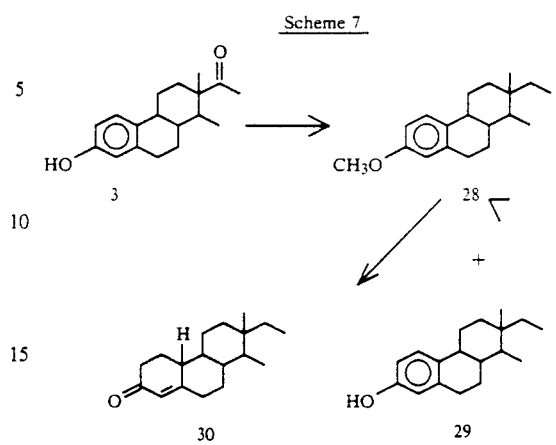

Scheme 7

To a three-neck round-bottom flask, equipped with a mechanical stirrer and dry ice condenser, was added 900 ml of ammonia while the flask was being cooled in a dry ice/acetone bath. To the ammonia was added 3.02 g of lithium wire (washed free of mineral oil with hexane). The solution turned dark blue as the lithium dissolved. After the addition of lithium was completed, the reaction was stirred an additional 1.0 hr at −78° C. To the dark blue solution was added 6.0 g of enone 7 in 150 ml of a dioxane ether solution (1:1). After stirring for 2.0 hr at −78° C., the reaction was quenched with the slow addition of sat. NH$_4$Cl. The reaction was allowed to warm to room temperature and the ammonia evaporated overnight. The white solid residue was dissolved in Et$_2$O/H$_2$O. The aqueous phase was separated and again washed with ether. The Et$_2$O solutions were combined and washed with H$_2$O. The Et$_2$O solutions were dried over MgSO$_4$ and evaporated at reduced pressure to afford 5.8 g of a crude mixture.

To a solution of 5.8 g of crude mixture containing 26 in 400 ml of acetone, cooled to 0°–5° C. (ice-water bath) with nitrogen bubbled into the acetone, was added dropwise Jones reagent until the solution's color remained a dark brown-orange. The reaction was stirred an additional 10 min at 0.5° C. and then quenched with the slow addition of 10 ml of isopropyl alcohol. The acetone was evaporated at reduced pressure, and the residue was dissolved in ether and water. The ether solution was separated and the aqueous phase was again extracted with ether. The ether solutions were combined and washed with water, dried over sodium sulfate, and evaporated at reduced pressure to yield 6.3 g of crude product. The crude product was chromatographed on 300 g of silica gel, 90–200 mesh, two-inch column, and eluted with 20% tetrahydrofuran/hexane to afford 4.1 g of pure 15,16-Seco-5α-19-norandrosta-3,17-dione (17). An analytical sample was obtained by recrystallization from ether/hexane, mp 76°–78° C.

Anal. Hi. Res. Mass Spec. for compound 27, C$_{18}$H$_{28}$O$_2$: Calcd., 276.2089; found, 276.2081. Calcd.: C, 78.21; H, 10.21. Found: C, 78.20; H, 9.95.

EXAMPLE 8

This example describes the synthesis of 15,16-secoestra-1,3,5(10)-triene,3-methyl ether (28) and 15,16-secoestra-1,3,5-trien-3ol (29) as outlined in Scheme 7:

(a.) 15,16-Secoestra-1,3,5(10)-triene, 3-methyl ether (28) and 15,16-secoestra-1,3,5-trien-3-ol (29): A suspension of 0.100 g of 3 in 10 ml of diethylene glycol and 1.0 ml of 64% hydrazine hydrate containing 0.2 g of potassium hydroxide was heated slowly (1.0 hr) to 200° C. A distillation head was used to collect the distillate at 110°–125° C. over 3.0 hr. The reaction was then heated for an additional 4 hr at 200° C., cooled poured into water, and extracted with ether. The ether solution was washed with water, 4% hydrochloric acid, and water, then was dried over magnesium sulfate and evaporated at reduced pressure to afford 0.071 g of crude product. The crude product was purified by thick-plate chromatography using a 1,000-µ thick plate developed in 10% tetrahydrofuran/hexane. Elution with ethyl acetate gave two fractions. Fraction. 1 contained 0.020 g of 28 and fraction 2, 0.028 g of 29.

Anal. Mass Spec. for compound C$_{19}$H$_{28}$O$_1$: Calcd., 272; found, 272. For compound 29, C$_{18}$H$_{26}$O$_1$: Calcd., 258; found, 258.

The same reaction conditions were used except that 7.0 g of 3, 150 ml of ethylene glycol, 70.0 ml of 64% hydrazine hydrate, and 10 g of potassium hydroxide were used to afford 6.2 g of product 29. Recrystallization from hexane afforded pure 29; mp 132°–133° C.

Anal. Hi. Res. Mass Spec. for compound C$_{18}$H$_{26}$O$_1$: Calcd., 258.1984; found, 258.2010.

(b.) 15,16-Secoestra-1,3,5(10)-triene, 3-methyl ether (28): A suspension of 5.1 g of 28 (as obtained in the preceding step) in 150 ml of acetone containing 5.0 g of potassium carbonate and 1.5 ml of methyl iodide was stirred at room temperature for 18 hr. The reaction mixture was poured into water and extracted with ether. The ether solution was washed with water several times, then dried over magnesium sulfate and evaporated at reduced pressure to afford 5.2 g of 28. Recrystallization from methanol afforded pure 28; mp 69°–70° C.

Anal Hi. Res. Mass Spec. for compound C$_{19}$H$_{28}$O: Calcd., 272.2140; found, 272.2129.

EXAMPLE 9

Synthesis of 15,16-seco-19-norandrosta-4-en-3-one (30):

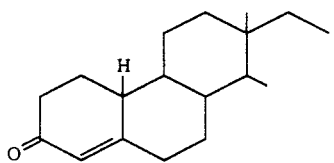

To a solution of 350 ml of ammonia at −78° C. (dry ice-acetone) was added 2.57 g of lithium wire, washed with of ether and 15 ml of absolute ethanol was added to the dark blue ammonia-lithium solution at −78° C. The reaction was stirred at −78° C. for an additional 2 hr while the dark blue color remained. The reaction was quenched with the slow addition of 200 ml of ethanol. The solution was allowed to warm to room temperature, and the ammonia was evaporated over 18 hr. The white solid residue was dissolved in ether and water, dried over sodium sulfate, and evaporated at reduced pressure to yield 4.2 g of an oil.

To a suspension of 4.2 g of the preceding oil in 150 ml of methanol was added dropwise 1.0 ml of concentrated hydrochloric acid. The reaction was stirred at room temperature for 18 hr. The methanol was evaporated to half its volume at reduced pressure and then poured into water. The milky suspension was extracted with ether. The ether solution was washed with water, dried over sodium sulfate, and evaporated to dryness at reduced pressure to afford 4.1 g of crude material. The crude material was purified on HPLC using 10% ethyl acetate and hexane, to afford 3.1 g of pure 15,16-seco-19-norandrosta-4-en-3-one (30). An analytical sample was obtained by recrystallization from methanol; mp 96°–97° C.

Anal. Hi. Res. Mass Spec. for compound $C_{18}H_{28}O$: Calcd., 260.2128; found, 260.2140.

EXAMPLE 10

This example describes the preparation of 15,16-seco-19-norandrosta-4,6-diene-3-one (34) according to Scheme 8:

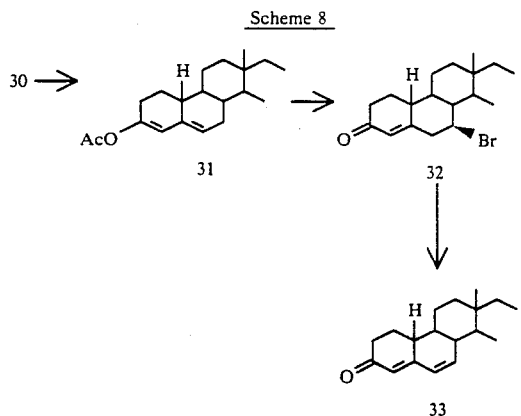

Scheme 8

(a.) 7β-Bromo-15,16-seco-19-norandrosta-4-ene-3-one (32): A solution of 2.15 g of 32 in 1.0 ml of acetic anhydride and 20.0 ml of freshly distilled acetyl chloride was refluxed for 4.0 hr. The solvent was removed at reduced pressure and the resulting oil was triturated with standing at 0°–10° C. for 18 hr, the white solid was collected by filtration and air dried for 18 hr. The solid was dissolved in ether and dried over magnesium sulfate, and the ether was evaporated at reduced pressure to afford 2.17 g of 31.

Anal Hi. Res. Mass Spec. for compound $C_{20}H_{30}O_2$: Calcd., 302; Found, 302.

To a solution of 2.17 g of 31 in 100 ml of acetone and 20 ml of water containing 3.0 ml of acetic acid, 1.4 ml of pyridine, and 2.81 g of sodium acetate at 0°–5° C. (ice water bath) was added 1.42 g of N-bromosuccinimide (recrystallized from water and dried over concentrated sulfuric acid at 0.01 mm Hg for three days). The reaction was stirred at 0°–5° C. for 3.0 hr while being shielded from the light with aluminum foil. The reaction mixture was poured into cold, saturated sodium chloride and extracted with ether. The ether solution was washed with. saturated sodium chloride, dried over magnesium sulfate, and evaporated at reduced pressure to afford 2.6 g of 32. Compound 32 was positive in the Beilstein test and was not further purified.

Anal. Mass Spec. for compound 32, $C_{18}H_{27}O$ Br: Calcd., 338; found, 338.

(b.) 15,16-Seco-19-norandrosta-4,6-diene-3-one (33): The bromoenone was dissolved in 30 ml of dimethylformamide and added to a boiling suspension of 2.5 g of lithium bromide and 2.5 g of lithium carbonate in 100 ml of dimethylformamide. The suspension was refluxed for 1.0 hr, then cooled and filtered. The filtrate was poured into an ice-water solution, and the mixture was extracted with ether. The ether solution was washed with 4% sodium hydroxide, water, and saturated sodium chloride. The ether solution was dried over magnesium sulfate and evaporated at reduced pressure to afford 1.87 g of 33. The mixture was purified on a Waters Prep 500 chromatograph using 10% ethyl acetate/hexane as the eluent, to afford 1.4 g of pure 33.

Anal. Hi. Res. Mass Spec. for compound $C_{18}H_{26}O$: Calcd., 258.1984; found, 258.1984.

EXAMPLE 11

This example describes the synthesis of 17α-acetoxy-15,16-seco-19-norandrosta-4-en-3-one (35) according to Scheme 9:

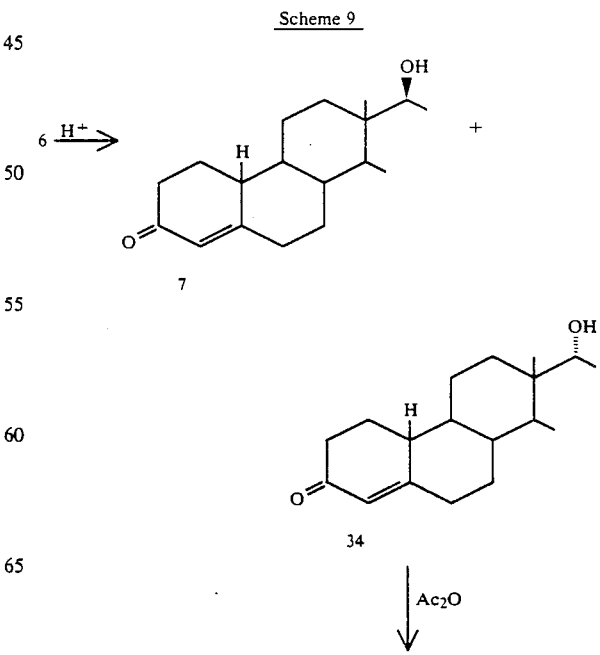

Scheme 9

-continued
Scheme 9

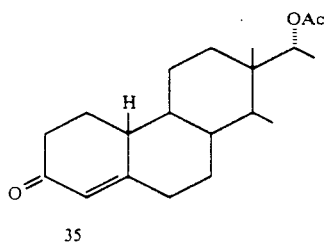
35

To a suspension of 11.16 g of 6 in 1.0 L of methanol was added dropwise 3.0 ml of concentrated hydrochloric acid. The reaction was stirred at room temperature for 18 hr. The methanol was evaporated to half its volume at reduced pressure and then poured into water. The milky suspension was extracted with ether. The ether solution was washed with water, dried over sodium sulfate, and evaporated to dryness at reduced pressure to afford 9.8 g of crude products 7 and 34. The crude products were crystallized from ether to yield 5.5 g of pure 7. The remaining material was purified on preparative HPLC, using 10% ethyl acetate/chloroform, to afford 1.4 g of 34.

A solution of 0.700 g of 34 in 10 ml of pyridine and 1.0 ml of acetic anhydride was stirred at room temperature for 18 hr. The reaction mixture was poured into ether/water and the organic phase was separated. The aqueous phase was extracted several times with ether. The ether solutions were combined, washed with water, 4%. hydrochloric acid, and water. The ether solution was dried over magnesium sulfate and evaporated at reduced pressure to yield 0.728 g of 35 as a glass. A similar run using 0.300 g of 34 afforded 0.298 g of product 35.

Anal. Hi. Res. Mass Spec. for compound 35, $C_{20}H_{30}O_3$: Calcd., 318.2195; found, 318.2217.

EXAMPLE 12

This example describes the synthesis of 17β-cyclobutyl-carboxylate-15,16-seco-19-norandrosta-4-en-3one (36) as in Scheme 10:

Scheme 10

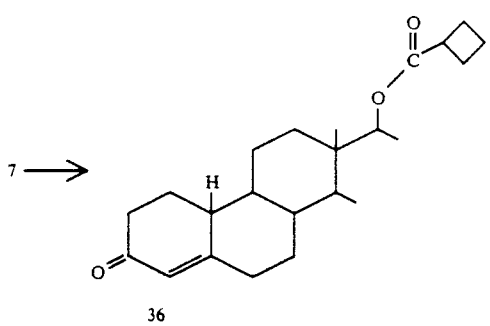
36

To a solution of 0.100 g of in 5.0 ml of pyridine was added, dropwise at 0°-5° C. (ice-water bath), 0.22 ml of cyclobutanecarboxylic acid chloride. The reaction was allowed to warm to room temperature and stirred for 18 hr. Then the reaction was poured into water and extracted with ether. The ether solution was washed with water, 4% sodium hydroxide, 4% hydrochloric acid, and water. The ether solution was dried over magnesium sulfate and evaporated at reduced pressure to afford 0.121 g of crude 36. The crude product was purified by thick-plate chromatography using 25% THF/hexane, to give 0.017 g of pure 36.

EXAMPLE 13

This example describes the preparation of 17β-(3',5'-dinitrobenzoate)-15,16-seco-19-norandrosta-4-en-3one (37) as shown in Scheme 11:

Scheme 11

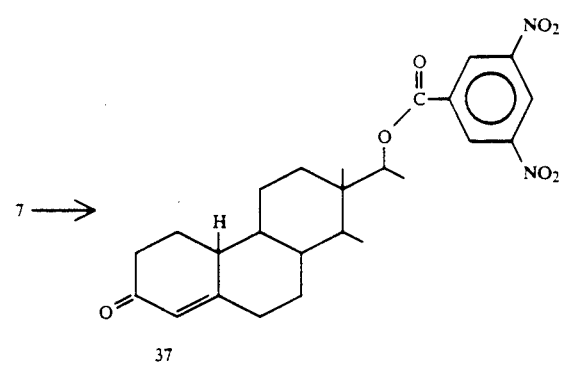
37

To a solution of 0.100 g of 7 in 5.0 ml of pyridine was added 0.094 g of 3,5-dinitrobenzoyl chloride. The reaction was stirred at room temperature for 18 hr. The reaction was then poured into water and extracted with ether. The ether solutions were combined and washed with water, saturated sodium bicarbonate, and water. The washed ether solution was dried over magnesium sulfate and evaporated at reduced pressure to afford 0.150 g of crude product 37. The crude product was purified by thick-plate chromatography, using 25% THF/hexane on a 2000-μ SiGF thick plate, to give 0.027 g of pure 37.

EXAMPLE 14

This example is directed to the synthesis of 17β-(2'-furoate)-15,16-seco-19-norandrosta-4-en-3-one (38) as shown in Reaction Scheme 12:

Scheme 12

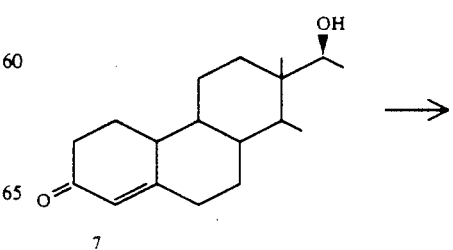
7

-continued
Scheme 12

The crude product was triturated from ether to afford 0.501 g of pure 38; mp 119°–120° C.

Anal. Hi. Res. Mass Spec. for compound 38, $C_{23}H_{30}O_4$: Calcd., 370.2139; found 370.2144.

EXAMPLE 15

This example describes preparation of 2α- and 2β-methyl derivatives via 17-tetrahydropyranyl ether intermediates as shown in Scheme 13.

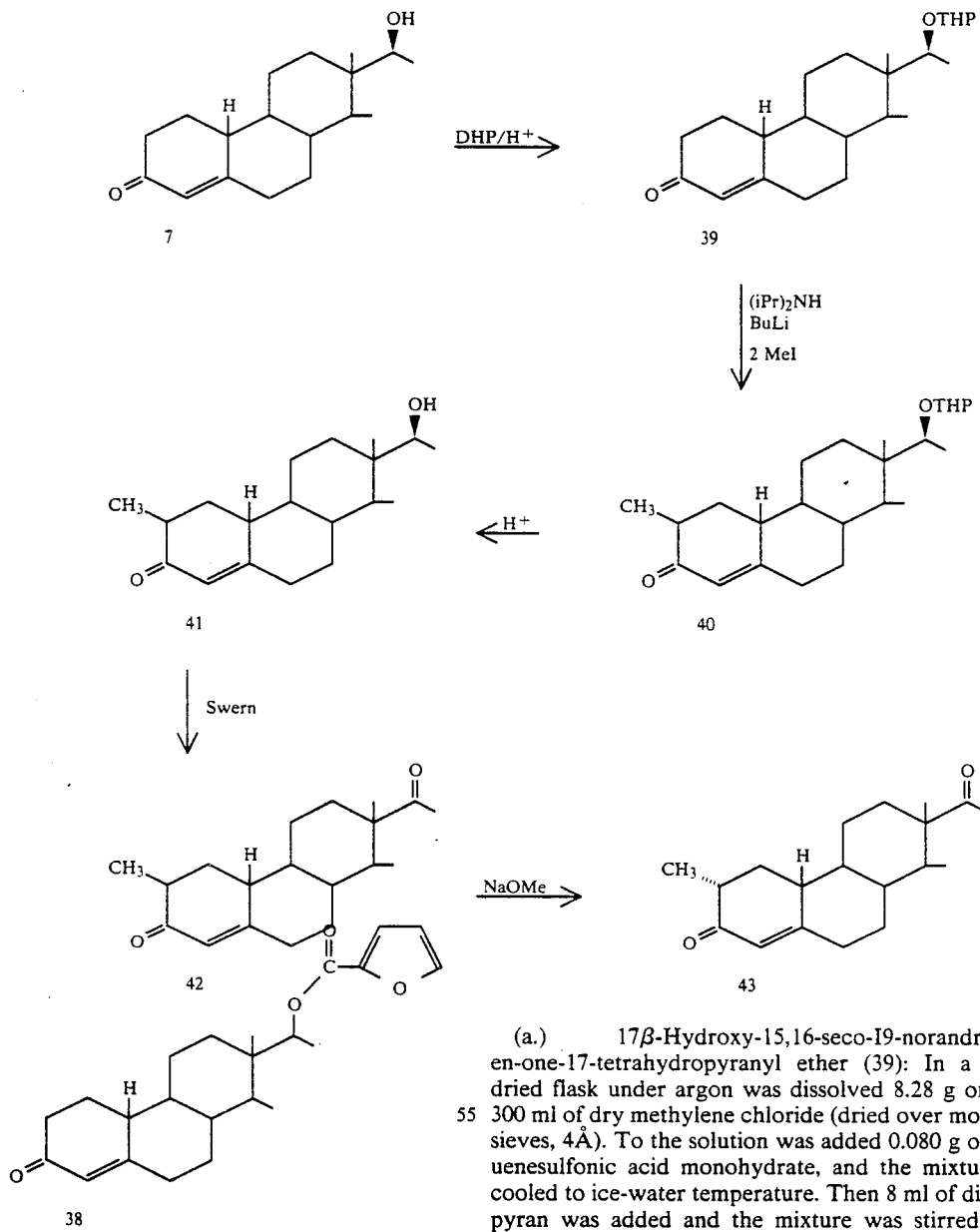

To a solution of 1.00 g of 7 in 30 ml of pyridine was added 0.04 ml of 2-furoyl chloride. The reaction was stirred at room temperature for 18 hr and then was poured into water and extracted with ether. The ether solutions were combined and washed with water, saturated sodium bicarbonate, and water. The ether solution was dried over magnesium sulfate and evaporated at reduced pressure to afford 0.980 g of crude product 38.

(a.) 17β-Hydroxy-15,16-seco-19-norandrosta-4-en-one-17-tetrahydropyranyl ether (39): In a flame-dried flask under argon was dissolved 8.28 g of (7) in 300 ml of dry methylene chloride (dried over molecular sieves, 4Å). To the solution was added 0.080 g of p-toluenesulfonic acid monohydrate, and the mixture was cooled to ice-water temperature. Then 8 ml of dihydropyran was added and the mixture was stirred under argon at ice-water temperature for 2 hr. Solid sodium bicarbonate (approximately 5 g) was added and the stirring was continued for 30 minutes while the solution warmed to room temperature. Dilution with 300 ml of ether, filtration through a Florisil (MCB 60–200 mesh), 600 g, 3-in. diameter column, and evaporation of the eluent yielded 6.82 g of the product 39. Further elution with 600 ml of methylene chloride-ether (50:50) yielded another 4.07 g of 39 for a total combined yield of 10.9 g.

(b.) 17β-Hydroxy-2β-methyl-15,16-seco-19-norandrosta-4-en-3-one-17-tetrahydropyranyl ether (40): Into a flame-dried reaction flask under argon was introduced 25 ml of dry tetrahydrofuran (dried by distillation from methyl magnesium bromide and storage over type 4Å molecular sieves) and a small amount of 2,2-dipyridyl was added. Next, 1.57M butyllithium in hexane was added until the solution turned reddish brown and the color persisted (at which time approximately 0.2 ml of the butyllithium solution had been added). 10.3 ml of the butyllithium solution was then added. The mixture was cooled to ice-water temperature, 3.79 ml of freshly distilled diisopropylamine was added, and the solution was stirred for 15 min. The mixture was cooled to between −75° C. and −80° C. (dry ice-acetate bath) and a solution of 4.0 g of 39 in 60 ml of dry tetrahydrofuran was added dropwise while the color of the reaction mixture was observed (the original reddish-brown color persisted after the addition of the steroid solution). The mixture was stirred at between −75° C. and −80° C. for 25 min, 10.2 ml of methyl iodide was added, the solution was allowed to warm to room temperature, and stirring was continued for 1 hr. The mixture was then added to saline water and the precipitate was extracted with ether. The combined ether extract was washed with saline and water, dried over sodium sulfate, and evaporated to dryness at reduced pressure, yielding 4 g of product 40, which was used in the following step without further purification.

(c.) 17β-hydroxy-2β-methyl-15,16-seco-19-norandrosta-4-en-3-one (41): Steroid 40 (4.0 g) was partially dissolved in 75 ml of 90% aqueous methanol and 30 ml of methylene chloride. Then 0.75 ml of concentrated hydrochloric acid was added, the mixture was stirred at room temperature for 2.5 hr. An additional 1.5 ml of concentrated hydrochloric acid was added and stirring continued for 90 minutes. TLC indicated that the reaction was complete. Most of the solvent was evaporated at reduced pressure at or below room temperature. The milky solution was diluted with water and extracted with ether. The combined ether extract was washed with saline water and with water, and then dried over sodium sulfate, and was evaporated to dryness at reduced pressure. This procedure afforded 3.06 g of product 41.

(d.) 2β-Methyl-15,16-seco-19-norandrosta-4-en-3,17-dione (42): Into a flame-dried flask under argon were introduced 6 ml of dry methylene chloride (dried by passing through a Woelm alumina, basic, activity grade Super I column and storage over 4Å molecular sieves) and 1.46 ml of freshly distilled oxalyl chloride. The solution was cooled to −78° (dry ice-acetone bath), and a solution of 2.46 ml of dry dimethylsulfoxide (dried over type 4Å molecular sieves) in 12 ml of dry methylene chloride was added dropwise during 2 min. The temperature was raised to −15° C. (ice-methanol bath) and the mixture stirred for 2 min. A solution of 3.03 g of steroid 41 in 24 ml of dry methylene chloride was added, the mixture was stirred at 15° C. for 15 min, followed by the addition of 10.2 ml of freshly distilled triethylamine. After stirring at −15° C. for 5 min, the reaction was allowed to warm to room temperature, and stirred for additional 30 min. To the reaction mixture was added 10 ml of water and additional methylene chloride. The separated aqueous layer was washed with methylene chloride. The combined methylene chloride extracts were washed with water, dried over sodium sulfate, and evaporated to dryness at reduced pressure. The residue. (3 g) was chromatographed on a Waters 500 preparative HPLC chromatograph on a normal-phase silica gel cartridge, using 5% ethyl acetate-chloroform, and 1.4 g of pure was obtained. One fraction was rechromatographed on a preparative HPLC, 1-inch stainless steel column packed with normal-phase silica gel. For elution, 10% ethyl acetatepetroleum ether (bp 35°-60° C.) was used. The product 42 was crystallized from ether-hexane to give an analytical sample; mp 100°-101° C.

Anal. Hi. Res. Mass Spec. for compound 42, $C_{19}H_{28}O_2$: Calcd., 288.2089; found, 288.2065.

(e.) 2β-Methyl-15,16-seco-19-norandrosta-4-en-3,17-dione (43): Sodium metal (70 mg) was dissolved in 10 ml of absolute methanol under argon at ice-water temperature. A solution of 0.582 g of 42 in 5 ml of absolute methanol was added, and the mixture was allowed to warm to room temperature and then stirred for 16 hr. TLC indicated the presence of starting material. Additional sodium methoxide (0.040 g) was added and the mixture was stirred for 4 hr, after which TLC indicated only a small amount of starting material. The mixture was added to saline water and the precipitate was extracted with ether. The combined ether extracts were washed with water, dried over sodium sulfate, and evaporated to dryness at reduced pressure. The crude residue (0.552 g) was chromatographed on a Waters 500 preparative HPLC chromatograph, using a 1-inch stainless steel column filled with normal-phase silica gel. Elution with 10% ethyl acetate-petroleum ether (bp 35°-60° C.) yielded 0.210 g of pure compound 43; mp 102°-103° C.

Anal. Hi. Res. Mass Spec. for compound $C_{19}H_{28}O_2$: Calcd., 288.2089; found, 288.2079.

EXAMPLE 16

This example describes the synthesis of a number of 13α-15,16-seco-progestins from 17-acetamido-3-methoxy-13α-estra-1,3,5(10)-16-tetraene as shown in Scheme 14.

SCHEME 14
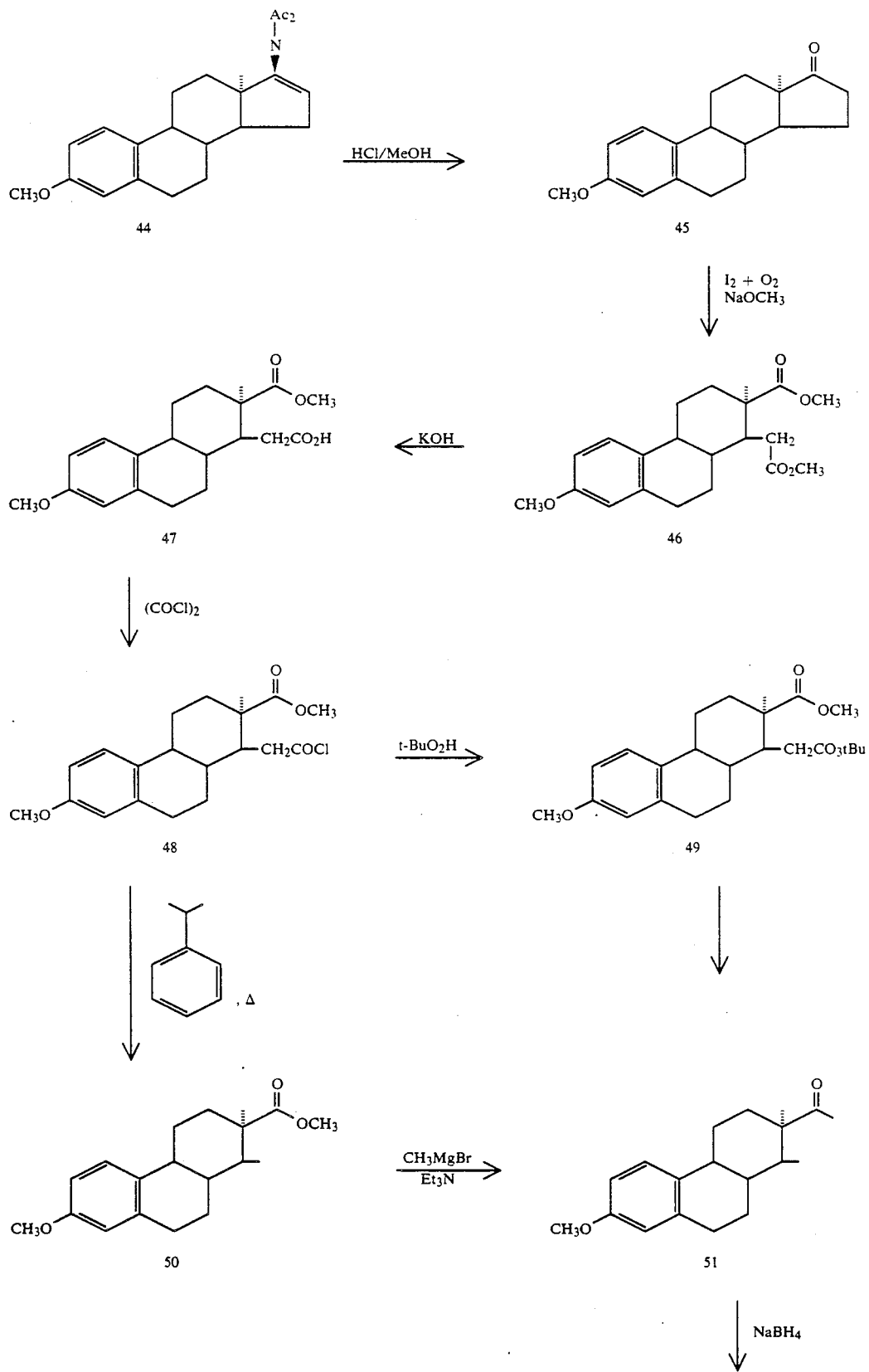

-continued
SCHEME 14

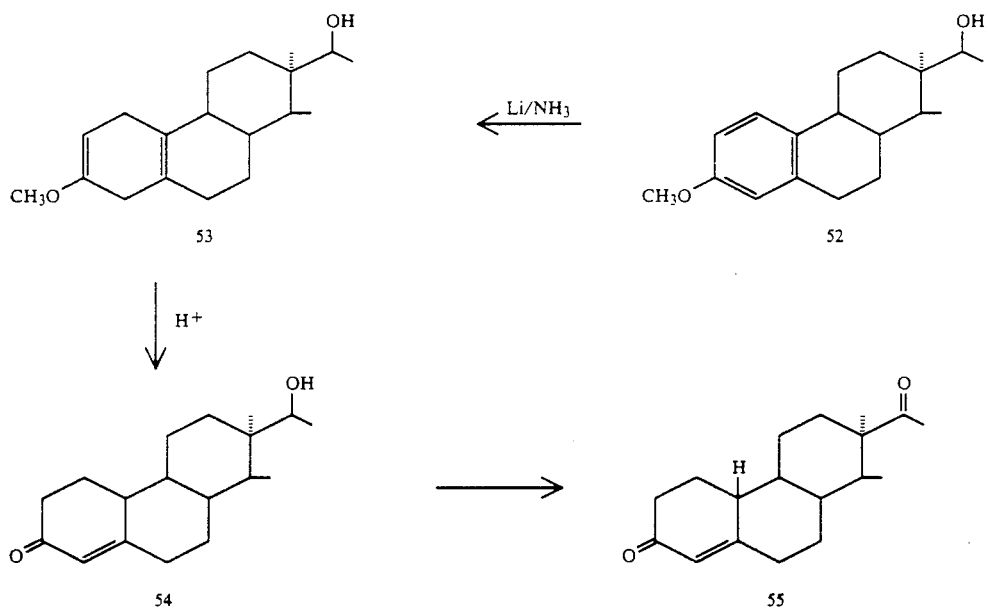

(a.) 3-Methoxy-13α-estra-1,3,5(10)-triene -17-one (45): To a solution of 15.5 g of 17-acetamido-3-methoxy-13α-estra-1,3,5(10)-16-tetraene (44); reported by D.H.R. Barton (R.B. Boar et al., *J. Chem. Soc.* Perkin I, 2163 (1977)) in 1200 ml of methanol was added 360 ml of 2N hydrochloric acid. The reaction mixture was refluxed for 1 hr. The methanol was evaporated at reduced pressure and then poured into water and ether. The organic phase was separated and the aqueous phase was extracted with additional ether. The ether fractions were combined, washed with water, dried over sodium sulfate, and evaporated at reduced pressure to afford 12.4 g of 45. An analytical sample was obtained by recrystallization from methanol; mp 128°-131° C., lit. mp 130°-133° C.

(b.) 3-Methoxy-16,17-seco-13α-estra-1,3,5(10)-triene-16,17-dioic acid dimethylester (46): A solution of sodium methoxide was prepared by dissolving 7.04 g of sodium in 1.54 ml of methanol. To this solution was added 10.0 g of 45, and the mixture was stirred for 1 hr to obtain a finely divided suspension. After cooling of the suspension to 0°-5° C. (ice bath), dry air was bubbled to obtain a saturated solution. (Dry air was obtained by first bubbling air into concentrated sulfuric acid, then passing it through a drying tube containing, in order: potassium hydroxide pellets, drierite, and calcium chloride.) A solution of 17.88 g of iodine in 161 ml of methanol was added dropwise (30 min) while the dry air was being bubbled in. After 3.0 hr of stirring at 5° C., the aeration and stirring were stopped and the flask was stored at 5° C. for 18 hr. The resulting yellow solution was acidified to approximately pH 3 with concentrate hydrochloric acid. The methanol was evaporated at reduced pressure to approximately 200 ml. The residue was taken up in ether and water, and the organic phase was separated. The aqueous phase was extracted several times with additional ether, and the ether extracts were combined The organic phase was washed with water, 10% sodium thiosulfate, and water. The ether was extracted with 4% sodium hydroxide. The ether solution was again washed with 10% sodium thiosulfate and water, dried over sodium sulfate, and evaporated to yield 6.194 g of diester (46). The sodium hydroxide extract was acidified with concentrated hydrochloric acid and extracted with ether. The ether solution was washed with water, dried over sodium sulfate, and evaporated at reduced pressure to yield 6.326 g of crude monoester (46A). The diester (46) was purified by thick-plate chromatography and recrystallized from methanol to afford pure (46), mp 92°-93° C.

Anal. Hi. Res. Mass Spec. for compound $C_{21}H_{28}O_5$: Calcd., 360.1939; found, 360.1937. Calcd.: C, 69.98; H, 7.83. Found: C, 69.79; H, 8.04.

(c.) 3-Methoxy-15,16-seco-13α-estra-1,3,5(10)-triene-16,17-dioic acid dimethylester (46): A solution of 6.4 g of (46A) in 50.0 ml of DMA containing 3.2 g of sodium bicarbonate and 3.0 ml of methyl iodide was stirred at room temperature for 18 hr. The reaction was poured into ether/water. The ether solution was separated, washed with 4% sodium hydroxide and water, dried over magnesium sulfate, and evaporated at reduced pressure to afford 6.483 g of 46.

(d.) 3-Methoxy-16,17-seco-13α-estra-1,3,5(10)-trien-16,17-dioic acid 17-methyl ester (47): To a warm solution of 1.0 g of 46 in 50 ml of methanol was added 1.28 g of potassium hydroxide in 50 ml of water. The solution was refluxed for 4 hr and then cooled. The methanol was evaporated to 10 ml and poured into water. The aqueous phase was extracted with ether. The ether was washed with water, dried over sodium sulfate, and evaporated at reduced pressure to yield 0.132 g of unreacted 46. The aqueous phases were combined, acidified with 18% hydrochloric acid, and extracted with ether. The ether solution was washed with water, dried over sodium sulfate, and evaporated at reduced pressure to yield 0.759 g of product 47. An analytical sample was obtained by thick-plate chromatography, using 35% tetrahydrofuran hexane and eluting with ethyl acetate. Recrystallization of 47 from hexane/acetone afforded pure 47; mp 131°-132° C.

Anal. Hi. Res. Mass Spec. for compound $C_{20}H_{26}O_5$: Calcd., 346.1780; found, 346.1809.

(e.) 3-Methoxy-16,17-seco-13α-estra-1,3,5(10)-triene-16,17-dioic acid 16-acid chloride 17-methyl ester (48): To 125 ml of dry benzene (dried over molecular sieves, Aldrich type 4Å) was added 6.3 g of 47. To the resulting solution, under argon, 6.2 ml of freshly distilled oxalyl chloride was added in two portions. The reaction mixture was then stirred at room temperature for 20 hr. The solvent and the excess oxalyl chloride were distilled off on a rotary evaporator. The residue 48 (6.4 g) was used in the following step without further purification.

(f.) 3-Methoxy-16,17-seco-13α-estra-1,3,5(10)-triene-16,17-dioic acid 16-t-butyl perester 17-methyl ester (49): To 122 ml of dry benzene (dried over molecular sieves, Aldrich, Type 4Å), was added 6.4 g of 48 from the preceding step. The solution was cooled in a cold-water bath to approximately 10° C. To the mixture, under argon, was added a mixture of 6.14 ml of freshly distilled tertbutylhydroperoxide and 13.46 ml of dry pyridine (dried over molecular sieves, Aldrich, Type 4Å). The cooling bath was removed, the mixture was allowed to warm to room temperature, and then was stirred for 2.5 hr. The solution was added to saturated sodium chloride solution and the organic layer was diluted with ether. The layers were separated and the aqueous layer was washed twice with ether. The combined organic extract was washed with 3% hydrochloric acid solution, 10% potassium hydroxide solution, and twice with saturated sodium chloride solution. The solution was then concentrated in vacuo to a viscous residue (7.4 g). The residue contained some impurities that did not interfere in the following reaction; therefore, the mixture 49 was used in the following step without further purification.

(g.) 3-Methoxy-16,17-seco-16-nor-13α-estra-1,3,5(10)-triene-17-oic acid methyl ester (50): A solution of 7.4 g of the residue 49 from the preceding reaction in 180 ml of freshly distilled cumene was purged with argon for 1 hr and was then heated to reflux temperature. The solution was heated at reflux temperature for 1 hr and then the solvent was distilled off in vacuo, to afford 7.04 g of residue. The residue was chromatographed on a Waters 500 preparative HPLC chromatograph. The product, compound 50, was eluted off with 10% ethyl acetate/ petroleum ether (bp 35°-60° C.). This procedure afforded 2.14 g of steroid 50.

Anal. Hi. Res. Mass Spec. for compound $C_{19}H_{26}O_3$: Calcd., 302.1882; found, 302.1879.

(h.) 3-Methoxy-15,16-seco-13α-estra-1,3,5(10)-triene-16-one (51): Under argon, 1.59 g of steroid 50 was dissolved in 21 ml of dry tetrahydrofuran (dried by distillation of methylmagnesium bromide and storage over molecular sieves, Aldrich type 4Å). To the solution was added 1.47 ml of dry triethylamine (dried by passing it through a column of Woelm alumina, basic, activity grade Super I). Then 10.5 ml of 3M methylmagnesium bromide was added. The mixture was stirred at room temperature for 120 hr and then added to 3% hydrochloric acid solution The products were extracted into three portions of ether. The combined ether extract was washed twice with water, dried over sodium sulfate, and evaporated to dryness at reduced pressure. A colorless oil (1.44 g) was obtained. The residue was chromatographed on a Waters 500 preparative HPLC chromatograph, using a 1-inch stainless steel column packed with normal-phase silica gel. The product was eluted off with 5% ethyl acetate/petroleum ether. This procedure afforded 0.527 g of compound 51. $C_{19}H_{26}O_6$: Calcd., 286.1933; found, 286.1918.

(i.) 3-Methoxy-17β-hydroxy-15,16-seco-13α-estra-1,3,5(10)-triene (52): A solution of 0.695 g of steroid 51 in 40 ml of absolute methanol was cooled in an ice-water bath to 0° C. Then 0.695 g of sodium borohydride was added to the solution in approximately 50 mg portions. The solution was stirred at ice-water temperature for 20 min and then poured into ice water. The precipitate was extracted into three portions of ether. The ether solution was washed three times with saturated sodium chloride solution, dried over sodium sulfate, and evaporated to dryness at reduced pressure. The oily residue, 0.634 g of compound 52, solidified on standing. The residue was used in the following step without further purification.

(j.) 17β-Hydroxy-15,16-seco-13α-estra-4-en-3one (53): Under argon, 60 ml of liquid ammonia was condensed at −78° C. (dry ice-acetone bath). Lithium wire (152 mg), cut into small pieces, was added and the mixture was stirred for 5 min. A solution of 0.634 g of 52 in 10 ml of dry THF (dried by distillation from methylmagnesium bromide and storage over molecular sieves, Aldrich 4Å) was added and the mixture stirred at −78° C. for 45 min. Then a mixture of 6 ml of absolute ethyl alcohol and 4 ml of dry THF was added. The cooling bath was removed and the blue color discharged after 15 min. The ammonia was allowed to evaporate and the residual solution was diluted first with ether and then with water The layers were separated and the aqueous layer was washed with ether. The combined ether extract was washed with water, dried over sodium sulfate, and evaporated to dryness at reduced pressure to afford 0.622 g of compound 53. The residue was homogeneous on thin-layer chromatographic analysis and was used in the following step without further purification.

The residue from the previous reaction, compound 53, was dissolved in 10 ml of absolute methanol and 0.5 ml. of water. Then 0.25 ml of concentrated hydrochloric acid was added and the mixture was heated to reflux temperature. After 20 min of gentle reflux, the solution was cooled to room temperature and neutralized with solid sodium acetate. Then the mixture was added to saturated sodium chloride solution and extracted into three portions of ether. The combined ether extract was washed twice with water, dried over sodium sulfate, and evaporated to dryness at reduced pressure to afford 0.945 g of compound 54, an oil that solidified on standing.

(k.) 15,16-Seco-13α-estra-4-en-3,17-dione (55): To a solution of 0.490 g of 54 in 50 ml of acetone at 0° C. (ice-water bath), with nitrogen being bubbled through the solution, was added dropwise Jones reagent until an orange-green color remained. Isopropanol was then added to quench excess Jones reagent. The acetone was evaporated at reduced pressure and the resulting residue was dissolved in ether and water. The ether solution was evaporated at reduced pressure to afford 0.425 g of crude product. The crude product was purified by thick-plate chromatography, using 25% THF/hexane and elution with ethyl acetate. Recrystallization from hexane afforded 0.075 g of pure 55.

Anal. Mass Spec. for 55, $C_{18}H_2O_2$: Calcd., 274.1933; found, 274.1930.

EXAMPLE 17

SCHEME 15

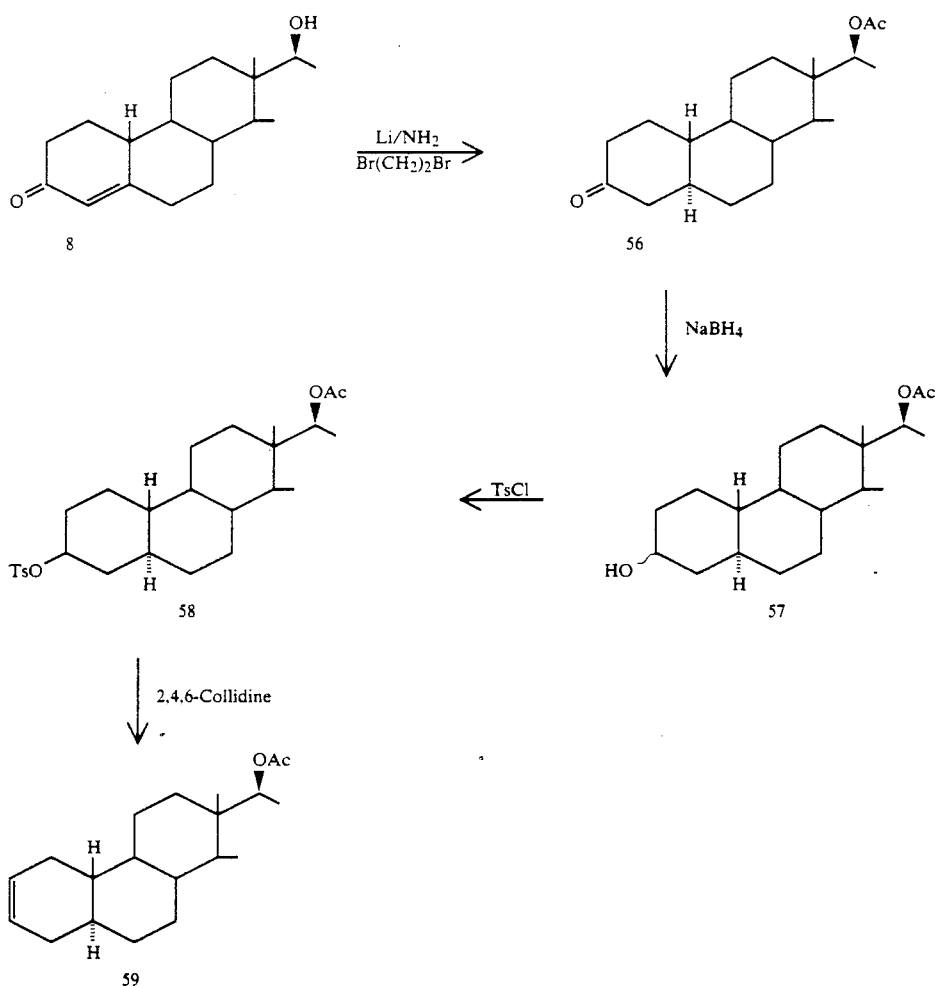

(a.) 17β-Acetoxy-15,16-seco-19-nor-5α-androstan-3-one (56): Into a flame-dried flask under argon, 300 ml of liquid ammonia was condensed at dry ice-acetone temperature (−75° to −80° C.). To the ammonia, 0.759 g of lithium wire was added. After the lithium dissolved, there was added a solution of 3.37 g of 8 in 100 ml of dry THF (dried by distillation from methyl magnesium bromide and stored over 4Å molecular sieves). The blue solution was stirred under argon at −75° C. for 1.0 hr. 1,2-dibromoethane was added dropwise to the solution until all the blue color had discharged. The ammonia was allowed to evaporate on removal of the cold bath. The residue was taken up in ether and saline water. The layers were separated and the aqueous layer was extracted with ether. The combined ether extract was washed with water, dried over MgSO₄, and concentrated to dryness at reduced pressure. The crude residue (3.98 g) was used in the following reaction without further purification.

The above mixture (3.98 g) was dissolved in 15 ml of dry pyridine (dried over KOH). To the solution, 4.0 ml of acetic anhydride was added and the mixture was stirred under argon at room temperature for 18 hr. The residue was dissolved in ether and water. The layers were separated and the aqueous layer was extracted with ether. The combined ether extract was washed with water, dried over MgSO₄, and evaporated to dryness at reduced pressure. The crude product (4.15 g) was purified by HPLC using a Waters Prep 500 with 8% ethyl acetate/petroleum ether. Evaporation at reduced pressure yielded 2.06 g of pure 56; mp 105°–107° C.

Anal. Hi. Res. Mass Spec. for 56, $C_{20}H_{32}O_3$: Calcd., 320.2352; found, 320.2351.

(b.) 17β-Acetoxy-15,16-seco-19-nor-5α -androstan-3ϵ-ol (57): To solution of 2.05 g of 56 in 200 ml of methanol at 0° C. (ice/water bath) was added 0.266 g of sodium borohydride in 0.075 g portions. The reaction was stirred for 2.0 hr at 0° C. and then quenched by the slow addition of 0.5 ml of acetic acid. The methanol was evaporated at reduced pressure and the resulting residue dissolved in ether and water. The ether solution was separated, washed with several portions of water, dried over magnesium sulfate, and evaporated at reduced pressure to afford 1.32 g of a C-3 mixture of β- and α-hydroxyls.

(c.) 17β-Acetoxy-15,16-seco-19-nor-5α-androstan-3-ol tosylate (58): To a solution of 1.32 g of 57 in 15 ml of dry pyridine (dried over KOH) was added 5.0 g of tosyl chloride. The reaction was stirred at room temperature for 18 hr and then poured into water and extracted with ether. The ether solution was washed with water, dried over magnesium sulfate, and evaporated at reduced pressure to yield 2.24 g of crude 58.

(d.) 17β-Acetoxy-15,16-seco-19-nor-5α-androsten-2-ene (59). A solution of 2.24 g of 58 in 50 ml of xylene and 50 ml of 2,3,6-collidine was refluxed for 3.0 hr. The reaction was cooled and poured into water. The suspension was extracted with ether. The ether solution was washed with water, 4% HCl, and water, then dried over magnesium sulfate and evaporated at reduced pressure to afford 1.91 g of crude product. Purification by thickplate chromatography using 20% THF/hexane afforded pure 59, mp 156°–159° C.

Anal. Hi. Res. Mass Spec. for 59, $C_{20}H_{32}O_2$: Calcd., 304.2402; found, 304.2407.

The following experimental methods were used in obtaining the data as set forth in Example 18, Table 2.

Progestin, androgen, and estrogen cytosol-binding assays were conducted as follows:

CYTOSOL-BINDING ASSAYS

Test for Binding of Steroid to Progesterone-Receptor Protein in Rabbit Uterus

Materials: The materials used in this assay were as follows: Progesterone-1,3,6,7-$^3$H (105 Ci/mmol), $^3$H-promegestone (80 Ci/mmol), and unlabeled promegestone, obtained from New England Nuclear Corp., Boston, Mass. (The purity of the compounds was guaranteed to be greater than 99% at delivery.) Unlabeled progesterone and activated charcoal were purchased from Sigma Chemical Company, St. Louis, Mo. Scintisol-Complete, was supplied by Isolab Inc., Akron, Oh.

Preparation of uterine cytosol (see E.M. Ritzen et al., Steroids 21:593 (1973) and A. Eisenfeld, Endocrinology 94:803 (1974): Uteri from immature New Zealand white female rabbits, weighing about 2 kg each, were chilled in ice immediately upon removal. After the fat was trimmed off, the uteri were minced and washed for 1 hour in Tris-HCl buffer (0.01M, pH 8.0, containing 0.001M EDTA and 0.25M sucrose) at 4° C. The washed uterine tissue was then homogenized in 2/5 (w/v) volume of the same Tris-HCl buffer. The homogenate was centrifuged at 12,000×g for 15 min, and the resulting supernatant was centrifuged again for 1 hour at 270,000×g. Glycerol was added to the final supernatant to give a 45% solution. The prepared cytosol was kept frozen until time of use. The whole procedure was carried out at approximately 4° C. The protein content of each prepared cytosol was determined by Biuret reagent.

Binding procedures: For the binding assay, 100 μl of uterine cytosol was mixed with 0.4 ml of Tris-HCl buffer (0.01M, pH 8.0, containing 0.001M EDTA, $^3$H-promegestone, and 1 μl of DMSO alone or 1 μl of DMSO plus competitors to be tested. The mixtures were incubated at 0°–4° C. for 24-hr. At the end of the incubation period, free and bound $^3$H-progesterone or $^3$H-promegestone were separated by charcoal extraction.

Charcoal extraction and scintillation counting: To the incubated mixture was added 0.5 ml of charcoal solution (300 mg of charcoal and 3 mg of Dextran 40 in 50 ml of Tris-HCl buffer used for homogenizing the tissue). The samples were mixed gently and incubated at 4° C. for exactly 10 min. The mixtures then were centrifuged at 4,000 rpm for 10 min in a refrigerated centrifuge. The supernatant containing the bound $^3$H-progesterone or $^3$H-promegestone was transferred quantitatively to a counting vial, and 10 ml of scintillation fluid (Scintisol) was added for counting. Counting time was adjusted to give a standard deviation of less than 10%. The scintillation counter used was either the Beckman LS-250 model or the Searle Mark III system. The efficiency for tritium on both counters was between 40 and 50%. The counts obtained for samples with competitors relative to those without competitors were calculated to give the percentage of competition.

2. Test for Binding of Steroids to Androgen-Binding Protein in Rat Testes

Materials: The materials used in this assay were as follows: Dihydrotestosterone-1,3-$^3$H (40 Ci/mmol), obtained from New England Nuclear Corp., Boston, Mass. (The purity of the compound was guaranteed to be greater than 98% at delivery.) Unlabeled dihydrotestosterone and activated charcoal were obtained from Sigma Chemical Company, St. Louis, Mo. Scintisol-Complete was purchased from Isolab Inc., Akron, Oh. The animals tested were mature Sprague-Dawley male rats.

Preparation of testicular cytosol: Immediately after the animals were sacrificed, their testes were removed and kept on ice. After the fat was trimmed off, the testes were minced and homogenized in three volumes of 0.01M Tris-HCl buffer (pH 8.0) containing 1.5 mM EDTA and 2 mM 2-mercaptoethanol. The homogenate was centrifuged at 100,000×g for 1 hr in a refrigerated centrifuge. The supernatant was transferred to a separate tube, and glycerol was added to make a 10% solution. The supernatant was then extracted with charcoal to remove the steroids that were already bound to the protein. For charcoal extraction, the supernatant was incubated with charcoal (3 mg/ml supernatant) at 0° C. to 4° C. for 18 hrs. The charcoal was then removed by centrifuging for 10 min at 12,000×g. The charcoal-extracted supernatant was kept frozen until time of use. Binding procedures: For the binding assay, 0.5 ml of testicular supernatant was mixed with 5 μl of DMSO containing 0.09 ng (27,500 dpm) of $^3$H -dihydrotestosterone and 10 μl of DMSO alone or 10 μl of DMSO plus competitors to be tested. The mixtures were incubated at 0°–4° C. for 3 hrs; then the free and bound $^3$H-dihydrotestosterone were separated by charcoal extraction.

Procedures for charcoal extraction and scintillation counting were the same as described for the progesterone binding assay.

3. In Vivo Estrogen Uterotropic Assay

Immature rats (18 days old) were assigned randomly to groups of 5 to 10. Treatment by oral incubation was started on the day the animals arrived and continued once daily for 4 days. On Day 5, vaginal smears were obtained, and uteri—carefully dissected between precise areas between the cervix and the oviduct—was stripped of fat and connective tissue and then weighed on a torsion balance. Fluid in uteri was expressed before weighing. Body weights of rats were recorded on the first day and at autopsy.

Comparison of the semilog dose-response curves for three to four dose levels of an active test compound with those for compounds of known activity (e.g., estrone administered sc or ethynyl estradiol given orally) determined the estrogenic activity.

4. Test for Androgenic Activity

Male 21-day-old rats were castrated upon their arrival. On the following day, they were distributed randomly in groups of 8. All animals were housed individually in a rack with ½-inch mesh, wire-bottom cages. The test compound was given by oral intubation for seven consecutive days and the test was performed on the day following the last treatment. Ventral prostates, seminal vesicles, and levator ani were freed of connective tissue and cleaned as they were being removed. They were then weighed to the nearest 0.2 mg on a torsion balance. Fluid from seminal vesicles was expressed before weighing. Body weights were recorded on the first day of injection and at autopsy. The degree of weight increase caused by the test compound was an indication of its androgenic activity.

Three or more dose levels of a test compound was compared with three standard doses of testosterone.

5. Test for Progestational Activity

In the Clauberg test, immature female rabbits weighing 800–1000 g, 3 rabbits for each dose, were primed subcutaneously with 0.5 μg estradiol in ml aqueous ethanol solution for 6 days to produce a suitable endometrium. The progestogen was then given subcutaneously in sesame oil for 7–11 days and the animals killed on day 12. The uterine horns were fixed in formalin, frozen sectioned and stained with haematoxylin and eosin. The degree of endometrial proliferation was estimated on the McPhail scale.

EXAMPLE 18

A number of the above tests were carried out on the compounds identified in Table 2. In Table 2, the Roman numeral identification system is as set forth earlier herein.

TABLE 2

| Nonradioactive Competitor | RBA (%) | Nonradioactive Competitor | RBA (%) |
|---|---|---|---|
| Promegestone | 194 | | |
| Progesterone | 100 | | |
| [structure] | 34 | [structure with NO2 groups] | 8.5 |
| [structure OAc] | 83 | [structure with furan] | 37 |
| [structure OAc with CH3] | 89 | [structure OAc with CN] | 38 |
| [structure] | 14 | [structure OAc] | 8.6 |

TABLE 2-continued

| Structure | Test | Total Dose | Potency |
|---|---|---|---|
| (steroid structure with OAc, CH₃, CH₃) | Clauberg | 1.0; 10 mg | 10–26% |

TABLE 2-continued

| Structure | Test | Dose | Result |
|---|---|---|---|
| (Steroid with OAc, CH₃, CH₃, CH₃ substituents) | Clauberg (Subc) | 0.1,0.1,0.4 1,10 mg | 200% |
| | Antigonadotropic (14 days) | 0.67 mg/day | 122% |
| | Uterotropic | 10,100;1000 μg | 0 |
| | Clauberg Oral | 1.0 & 10 mg | 2.4–6.8% |
| | Androgenic Subc | 1.0 mg | 0 |
| | Androgenic Oral | 1.0 & 10 mg | 0 |
| | Postcoital | 1.0 mg/day subc | 10/10 pregnant |
| (Steroid with C(=O), CH₃, CH₃ substituents) | Clauberg Subc | 1.0 & 10 mg | 16–57% |
| (Steroid with OAc, CH₃, CH₃ substituents, Δ6) | Postcoital (0–4 days) | 1.0 mg/day Subc | 9/10 pregnant |
| (Steroid with OAc, CH₃, CH₃, CN substituents) | Clauberg | 0.2,0.4,0.8 mg | 101 |
| (Steroid with furoate ester, CH₃) | Clauberg | 1.0;10 mg | 8.0% at 10 mg |
| (Steroid with C(=O), CH₃, aromatic A-ring, HO-) | Uterotropic | 1.0; 100 μg | 0 |
| (Steroid with OH, C≡CH, CH₃) | Clauberg | | 8.0% |

| | | |
|---|---|---|
| 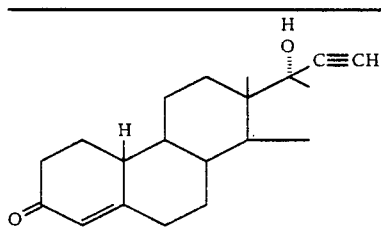 | Clauberg | 8.0% |

In Table 2, "RBA" represents relative binding affinity, i.e., the concentration of the compound under evaluation that is required to displace 50% of the bound radioactivity of promogestone divided by the concentration of promogestone required to obtain the same displacement.

Under the column "standard" in Table 2, "a" designates that the standard used in the above-described Clauberg test was progesterone. The standard represented by "b" is estradiol, while those designated "c," "d" and "e" are ethynylestradiol, testosterone, and levonor-gestrel, respectively.

Under the column "in vivo biological test", "f" represents the Clauberg assay of T. Miyake at page 135 of "Methods in Hormone Research," vol. II, ed. R.I. Dorfman (New York: Academic Press, 1962). The androgenic assay performed was that of R.I. Dorfman, also in "Methods in Hormone Research," vol. II, at page 305. The antigonadotropic assay was carried out according to the method of E.G. Shipley, id. at page 59.

We claim:

1. A compound having the formula (Ia) or (Ib):

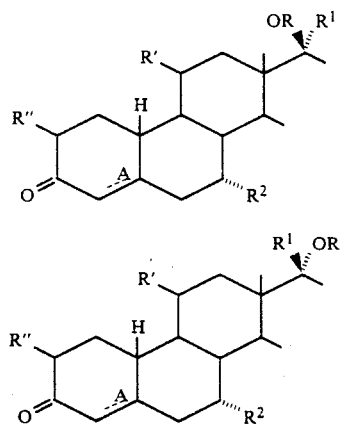

wherein:

R is hydrogen or an acyl group of the formula —(C=O)—Y;

Y is an organic substituent selected from the group consisting of alkyl, alkenyl, alkynyl, cycloalkyl, cycloalkylalkylene, haloalkyl, aryl, haloaryl and arylalkylene;

R' is hydrogen or, alkyl of 1 to 12 carbon atoms, or

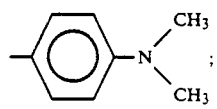

R" is hydrogen or lower alkyl;

$R^1$ is selected from the group consisting of hydrogen, alkyl, alkenyl and alkynyl;

$R^2$ is selected from the group consisting of hydrogen, lower alkyl, and cyano; and A represents an optional double bond.

2. The compound of claim 1 having the structure of formula (Ia).

3. The compound of claim 1 having the structure of formula (Ib).

4. The compound of claim 2 wherein:

R is hydrogen or an acyl group of the formula —(C=O)—Y;

R' and R" are hydrogen;

Y is selected from the group consisting of: lower alkyl; cycloakyl; phenyl optionally substituted with 1 or lower alkyl, lower alkoxy, hydroxy and/or nitro substituents; and $R^1$ is hydrogen or lower alkynyl.

5. The compound of claim 4 wherein:

R is —(C=O)—Y;

Y is selected from the group consisting of methyl, cyclobutyl, 3,5-dinitrophenyl;

$R^1$ is hydrogen or —C≡CH;

$R^2$ is hydrogen, methyl or cyano; and

A represents a double bond.

6. The compound of claim 5 which is 17β-acetoxy-17α-methyl-15,16-seco-19-norandrosta-4-en-3-one.

7. The compound of claim 3 wherein:

R is hydrogen or an acyl group of the formula —(C=O)—Y;

R' and R" are hydrogen;

Y is selected from the group consisting of: lower alkyl; cycloalkyl; phenyl optionally substituted with 1 or lower alkyl, lower alkoxy, hydroxy and/or nitro substituents; and $R^1$ is hydrogen or lower alkynyl.

8. The compound of claim 7 wherein:

R is —(C=O)—Y;

Y is selected from the group consisting of methyl, cyclobutyl, 3,5-dinitrophenyl;

$R^1$ is hydrogen or —C≡CH;

$R^2$ is hydrogen, methyl or cyano; and

A represents a double bond.

9. A pharmaceutical composition useful for the suppression of ovulation in a human female, comprising a fertility-controlling effective amount of the compound of claim 1, in admixture with a pharmaceutically acceptable excipient.

10. The pharmaceutical composition of claim 9, further comprising an effective extrogenic amount of a compound selected from the group consisting of ethynyl estradiol, estradiol valerate, estradiol cyprionate, estradiol decanoate, and estradiol acetate.

11. A method of contraception in female mammals, which method comprises administering to such mammal a fertility-controlling effective amount of a compound of claim 1, or a pharmaceutical composition containing such a compound.

* * * * *